United States Patent
Truncale et al.

(10) Patent No.: US 7,901,457 B2
(45) Date of Patent: *Mar. 8, 2011

(54) CARTILAGE ALLOGRAFT PLUG

(75) Inventors: Katherine Gomes Truncale, Hillsborough, NJ (US); Arthur A. Gertzman, Flemington, NJ (US); Moon Hae Sunwoo, Old Tappan, NJ (US); William W. Tomford, Belmont, MA (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 131 days.

This patent is subject to a terminal disclaimer.

(21) Appl. No.: 10/438,883

(22) Filed: May 16, 2003

(65) Prior Publication Data

US 2004/0230303 A1    Nov. 18, 2004

(51) Int. Cl.
*A61F 2/28* (2006.01)
(52) U.S. Cl. ...................................... 623/16.11
(58) Field of Classification Search ............... 623/11.11, 623/16.11, 17.11, 17.16, 23.56, 23.57, 23.58, 623/23.59, 23.6, 23.61, 23.62, 23.63, 14.12, 623/20.14

See application file for complete search history.

(56) References Cited

U.S. PATENT DOCUMENTS

| | | | |
|---|---|---|---|
| 3,400,199 A | 9/1968 | Balassa | |
| 3,551,560 A | 12/1970 | Theile | |
| 3,772,432 A | 11/1973 | Balassa | |
| 3,867,728 A | 2/1975 | Stubstad et al. | |
| 3,966,908 A | 6/1976 | Balassa | |
| 4,060,081 A | 11/1977 | Yannas et al. | |
| 4,172,128 A | 10/1979 | Thiele et al. | |
| 4,201,845 A | 5/1980 | Feder et al. | |
| 4,296,100 A | 10/1981 | Franco | |
| 4,378,347 A | 3/1983 | Franco | |
| 4,394,370 A | 7/1983 | Jefferies | |
| 4,400,833 A | 8/1983 | Kurland | |
| 4,442,655 A | 4/1984 | Stroetmann | |
| 4,458,678 A | 7/1984 | Yannas et al. | |
| 4,479,271 A | 10/1984 | Bolesky et al. | |
| 4,501,269 A * | 2/1985 | Bagby ........................ 606/61 |
| 4,505,266 A | 3/1985 | Yannas et al. | |
| 4,600,574 A | 7/1986 | Lindner et al. | |
| 4,627,853 A | 12/1986 | Campbell et al. | |

(Continued)

FOREIGN PATENT DOCUMENTS

EP    0517030 A2    12/1992

(Continued)

OTHER PUBLICATIONS

Translation of WO 99/21497 A1.*

(Continued)

*Primary Examiner* — Anu Ramana
(74) *Attorney, Agent, or Firm* — Greenberg Traurig, LLP

(57) ABSTRACT

The invention is directed toward a cartilage repair assembly comprising a shaped allograft structure of subchondral bone with an integral overlying cartilage cap which is treated to remove cellular debris and proteoglycans and milled allograft cartilage in a bioabsorbable carrier. The shaped structure is dimensioned to fit in a drilled bore in a cartilage defect area so that either the shaped bone or the cartilage cap engage the side wall of the drilled bore in an interference fit and is in contact with a milled cartilage and biocompatible carrier mixture allowing cell transfer throughout the defect area. A method for inserting the shaped allograft structure into a cartilage defect area is also disclosed.

2 Claims, 2 Drawing Sheets

U.S. PATENT DOCUMENTS

| | | |
|---|---|---|
| 4,642,120 A | 2/1987 | Nevo et al. |
| 4,656,137 A | 4/1987 | Balassa |
| 4,681,763 A | 7/1987 | Nathanson et al. |
| 4,683,195 A | 7/1987 | Mullis et al. |
| 4,683,202 A | 7/1987 | Mullis |
| 4,757,017 A | 7/1988 | Cheung |
| 4,776,173 A | 10/1988 | Kamarei et al. |
| 4,776,853 A | 10/1988 | Klement et al. |
| 4,795,467 A | 1/1989 | Piez et al. |
| 4,801,299 A | 1/1989 | Brendel et al. |
| 4,837,379 A | 6/1989 | Wienberg |
| 4,846,835 A | 7/1989 | Grande |
| 4,880,429 A | 11/1989 | Stone |
| 4,902,508 A | 2/1990 | Badylak et al. |
| 4,904,259 A | 2/1990 | Itay |
| 4,932,973 A | 6/1990 | Gendler |
| 4,950,296 A | 8/1990 | McIntyre |
| 4,950,483 A | 8/1990 | Ksander et al. |
| 4,955,911 A | 9/1990 | Frey et al. |
| 4,963,146 A | 10/1990 | Li |
| 4,965,188 A | 10/1990 | Mullis et al. |
| 4,971,954 A | 11/1990 | Brodsky et al. |
| 4,976,738 A | 12/1990 | Frey et al. |
| 4,978,355 A | 12/1990 | Frey et al. |
| 4,994,559 A | 2/1991 | Moscatelli et al. |
| 5,002,583 A | 3/1991 | Pitaru et al. |
| 5,007,934 A | 4/1991 | Stone |
| 5,041,138 A | 8/1991 | Vacanti et al. |
| 5,053,049 A | 10/1991 | Campbell |
| 5,053,050 A | 10/1991 | Itay |
| 5,067,964 A | 11/1991 | Richmond et al. |
| 5,073,373 A | 12/1991 | O'Leary et al. |
| 5,084,051 A | 1/1992 | Tormala et al. |
| 5,118,512 A | 6/1992 | O'Leary et al. |
| 5,152,791 A | 10/1992 | Hakamatsuka et al. |
| 5,155,214 A | 10/1992 | Baird et al. |
| 5,191,067 A | 3/1993 | Lappi et al. |
| 5,195,892 A * | 3/1993 | Gersberg ............... 433/174 |
| 5,206,023 A | 4/1993 | Hunziker |
| 5,236,456 A * | 8/1993 | O'Leary et al. ............ 623/23.63 |
| 5,256,140 A | 10/1993 | Fallick |
| 5,260,420 A | 11/1993 | Burnouf-Radosevich et al. |
| 5,266,476 A | 11/1993 | Sussman et al. |
| 5,270,300 A | 12/1993 | Hunziker |
| 5,275,826 A | 1/1994 | Badylak et al. |
| 5,284,155 A | 2/1994 | Treadwell et al. |
| 5,290,558 A | 3/1994 | O'Leary et al. |
| 5,298,254 A | 3/1994 | Prewett et al. |
| 5,302,702 A | 4/1994 | Seddon et al. |
| 5,306,304 A | 4/1994 | Gendler |
| 5,306,311 A | 4/1994 | Stone et al. |
| 5,310,883 A | 5/1994 | Seddon et al. |
| 5,314,476 A | 5/1994 | Prewett et al. |
| 5,326,357 A | 7/1994 | Kandel |
| 5,329,846 A | 7/1994 | Bonutti |
| 5,336,616 A | 8/1994 | Livesey et al. |
| 5,338,772 A | 8/1994 | Bauer et al. |
| 5,352,463 A | 10/1994 | Badylak et al. |
| 5,354,557 A | 10/1994 | Oppermann et al. |
| 5,356,629 A | 10/1994 | Sander et al. |
| 5,368,858 A | 11/1994 | Hunziker |
| 5,380,328 A | 1/1995 | Morgan |
| 5,411,885 A | 5/1995 | Marx |
| 5,425,769 A | 6/1995 | Snyders, Jr. |
| 5,439,684 A | 8/1995 | Prewett et al. |
| 5,439,818 A | 8/1995 | Fiddes et al. |
| 5,443,950 A | 8/1995 | Naughton et al. |
| 5,464,439 A | 11/1995 | Gendler |
| 5,466,462 A | 11/1995 | Rosenthal et al. |
| 5,491,220 A | 2/1996 | Seddon et al. |
| 5,496,722 A | 3/1996 | Goodwin et al. |
| 5,507,813 A | 4/1996 | Dowd et al. |
| 5,512,460 A | 4/1996 | Nauro et al. |
| 5,513,662 A | 5/1996 | Morse et al. |
| 5,516,532 A | 5/1996 | Atala et al. |
| 5,545,222 A | 8/1996 | Bonutti |
| 5,556,430 A | 9/1996 | Gendler |
| 5,569,272 A | 10/1996 | Reed et al. |
| 5,571,895 A | 11/1996 | Kurokawa et al. |
| 5,576,288 A | 11/1996 | Lappi et al. |
| 5,604,293 A | 2/1997 | Fiddes et al. |
| 5,607,474 A | 3/1997 | Athanasiou et al. |
| 5,614,496 A | 3/1997 | Dunstan et al. |
| 5,618,925 A | 4/1997 | Dupont et al. |
| 5,622,928 A | 4/1997 | Naruo et al. |
| 5,624,463 A | 4/1997 | Stone et al. |
| 5,631,011 A | 5/1997 | Wadstrom |
| 5,632,745 A | 5/1997 | Schwartz |
| 5,656,598 A | 8/1997 | Dunstan et al. |
| 5,662,710 A | 9/1997 | Bonutti |
| 5,679,637 A | 10/1997 | Lappi et al. |
| 5,695,998 A | 12/1997 | Badylak et al. |
| 5,700,476 A | 12/1997 | Rosenthal et al. |
| 5,700,774 A | 12/1997 | Hattersley et al. |
| 5,707,962 A | 1/1998 | Chen et al. |
| 5,713,374 A | 2/1998 | Pachence et al. |
| 5,716,413 A | 2/1998 | Walter et al. |
| 5,723,331 A | 3/1998 | Tubo et al. |
| 5,736,372 A | 4/1998 | Vacanti et al. |
| 5,749,874 A | 5/1998 | Schwartz |
| 5,759,190 A | 6/1998 | Vibe-Hansen et al. |
| 5,769,899 A | 6/1998 | Schwartz et al. |
| 5,770,417 A | 6/1998 | Vacanti et al. |
| 5,782,835 A | 7/1998 | Hart et al. |
| 5,782,915 A | 7/1998 | Stone |
| 5,786,217 A | 7/1998 | Tubo et al. |
| 5,800,537 A | 9/1998 | Bell |
| 5,814,084 A * | 9/1998 | Grivas et al. ............... 623/23.48 |
| 5,842,477 A | 12/1998 | Naughton et al. |
| 5,846,931 A | 12/1998 | Hattersley et al. |
| 5,853,746 A | 12/1998 | Hunziker |
| 5,855,620 A | 1/1999 | Bishopric et al. |
| 5,859,208 A | 1/1999 | Fiddes et al. |
| 5,863,296 A | 1/1999 | Orton |
| 5,863,297 A | 1/1999 | Walter et al. |
| 5,866,415 A | 2/1999 | Villeneuve |
| 5,876,452 A | 3/1999 | Athanasiou et al. |
| 5,888,219 A | 3/1999 | Bonutti |
| 5,893,888 A | 4/1999 | Bell |
| 5,899,936 A | 5/1999 | Goldstein |
| 5,899,939 A | 5/1999 | Boyce et al. |
| 5,904,716 A | 5/1999 | Gendler |
| 5,906,827 A | 5/1999 | Khouri et al. |
| 5,910,315 A | 6/1999 | Stevenson et al. |
| 5,916,265 A | 6/1999 | Hu |
| 5,948,429 A | 9/1999 | Bell et al. |
| 5,955,438 A | 9/1999 | Pitaru et al. |
| 5,972,368 A * | 10/1999 | McKay ..................... 424/423 |
| 5,972,385 A | 10/1999 | Liu et al. |
| 5,974,663 A | 11/1999 | Ikeda et al. |
| 5,989,269 A | 11/1999 | Vibe-Hansen et al. |
| 5,989,289 A | 11/1999 | Coates et al. |
| 5,989,866 A | 11/1999 | Deisher et al. |
| 5,998,170 A | 12/1999 | Arakawa et al. |
| 6,001,352 A | 12/1999 | Boyan et al. |
| 6,005,161 A | 12/1999 | Brekke et al. |
| 6,013,853 A | 1/2000 | Athanasiou et al. |
| 6,017,348 A | 1/2000 | Hart et al. |
| 6,025,334 A | 2/2000 | Dupont et al. |
| 6,025,538 A | 2/2000 | Yaccarino, III |
| 6,027,743 A | 2/2000 | Khouri et al. |
| 6,030,635 A | 2/2000 | Gertzman et al. |
| 6,037,171 A | 3/2000 | Larsson |
| 6,039,762 A | 3/2000 | McKay |
| 6,060,640 A | 5/2000 | Pauley et al. |
| 6,074,663 A | 6/2000 | Delmotte et al. |
| 6,080,194 A | 6/2000 | Pachence et al. |
| 6,090,996 A | 7/2000 | Li |
| 6,090,998 A | 7/2000 | Grooms et al. |
| 6,096,081 A | 8/2000 | Grivas et al. |
| 6,096,347 A | 8/2000 | Geddes et al. |
| 6,110,209 A | 8/2000 | Stone |
| 6,110,482 A | 8/2000 | Khouri et al. |
| 6,123,731 A | 9/2000 | Boyce et al. |
| 6,132,472 A | 10/2000 | Bonutti |
| 6,143,293 A | 11/2000 | Weiss et al. |
| 6,156,068 A | 12/2000 | Walter et al. |

| | | |
|---|---|---|
| 6,165,486 A | 12/2000 | Marra et al. |
| 6,165,487 A | 12/2000 | Ashkar et al. |
| 6,180,605 B1 | 1/2001 | Chen et al. |
| 6,183,737 B1 | 2/2001 | Zaleske et al. |
| 6,189,537 B1 | 2/2001 | Wolfinbarger, Jr. |
| 6,197,586 B1 | 3/2001 | Bhatnagar et al. |
| 6,200,347 B1 | 3/2001 | Anderson et al. |
| 6,221,854 B1 | 4/2001 | Radomsky |
| 6,231,607 B1 | 5/2001 | Ben-Bassat et al. |
| 6,235,316 B1 | 5/2001 | Adkisson |
| 6,242,247 B1 | 6/2001 | Rieser et al. |
| 6,251,143 B1 | 6/2001 | Schwartz et al. |
| 6,258,778 B1 | 7/2001 | Rodgers et al. |
| 6,261,586 B1 | 7/2001 | McKay |
| 6,267,786 B1 | 7/2001 | Stone |
| 6,270,528 B1 | 8/2001 | McKay |
| 6,274,090 B1 | 8/2001 | Coelho et al. |
| 6,274,663 B1 | 8/2001 | Hosokawa et al. |
| 6,274,712 B1 | 8/2001 | Springer et al. |
| 6,280,473 B1 | 8/2001 | Lemperle et al. |
| 6,281,195 B1 | 8/2001 | Rueger et al. |
| 6,283,980 B1 | 9/2001 | Vibe-Hansen et al. |
| 6,293,970 B1 | 9/2001 | Wolfinbarger, Jr. |
| 6,294,187 B1 | 9/2001 | Boyce et al. |
| 6,294,359 B1 | 9/2001 | Fiddes et al. |
| 6,303,585 B1 | 10/2001 | Spiro et al. |
| 6,305,379 B1 | 10/2001 | Wolfinbarger, Jr. |
| 6,306,174 B1 | 10/2001 | Gie et al. |
| 6,306,424 B1 | 10/2001 | Vyakarnam et al. |
| 6,310,267 B1 | 10/2001 | Rapp |
| 6,319,712 B1 | 11/2001 | Meenen et al. |
| 6,333,029 B1 | 12/2001 | Vyakarnam et al. |
| 6,352,558 B1 | 3/2002 | Spector |
| 6,352,971 B1 | 3/2002 | Deisher et al. |
| 6,361,565 B1 | 3/2002 | Bonutti |
| 6,376,244 B1 | 4/2002 | Atala |
| 6,379,367 B1 | 4/2002 | Vibe-Hansen et al. |
| 6,379,385 B1 | 4/2002 | Kalas et al. |
| 6,383,221 B1 | 5/2002 | Scarborough et al. |
| 6,387,693 B2 | 5/2002 | Rieser et al. |
| 6,398,811 B1 | 6/2002 | McKay |
| 6,398,816 B1 | 6/2002 | Breitbart et al. |
| 6,398,972 B1 | 6/2002 | Blasetti et al. |
| 6,432,436 B1 | 8/2002 | Gertzman et al. |
| 6,437,018 B1 | 8/2002 | Gertzman et al. |
| 6,440,141 B1 * | 8/2002 | Philippon ............ 606/99 |
| 6,440,427 B1 | 8/2002 | Wadstrom |
| 6,440,444 B2 | 8/2002 | Boyce et al. |
| 6,454,811 B1 | 9/2002 | Sherwood et al. |
| 6,458,144 B1 | 10/2002 | Morris et al. |
| 6,458,158 B1 | 10/2002 | Anderson et al. |
| 6,458,375 B1 | 10/2002 | Gertzman et al. |
| 6,468,314 B2 | 10/2002 | Schwartz |
| 6,471,993 B1 | 10/2002 | Shastri et al. |
| 6,475,175 B1 | 11/2002 | Rivera et al. |
| 6,486,377 B2 | 11/2002 | Rapp |
| 6,488,033 B1 | 12/2002 | Cerundolo |
| 6,489,165 B2 | 12/2002 | Bhatnagar |
| 6,497,726 B1 | 12/2002 | Carter et al. |
| 6,503,277 B2 | 1/2003 | Bonutti |
| 6,511,511 B1 | 1/2003 | Slivka et al. |
| 6,511,958 B1 | 1/2003 | Atkinson et al. |
| 6,514,514 B1 | 2/2003 | Atkinson et al. |
| 6,520,964 B2 * | 2/2003 | Tallarida et al. ............ 606/71 |
| 6,530,956 B1 | 3/2003 | Mansmann |
| 6,534,084 B1 | 3/2003 | Vyakarnam et al. |
| 6,541,024 B1 | 4/2003 | Kadiyala et al. |
| 6,548,729 B1 | 4/2003 | Seelich et al. |
| 6,569,172 B2 | 5/2003 | Ascalai et al. |
| 6,576,015 B2 | 6/2003 | Geistlich et al. |
| 6,582,960 B1 | 6/2003 | Martin et al. |
| 6,591,581 B2 | 7/2003 | Schmieding |
| 6,592,598 B2 | 7/2003 | Vibe-Hansen et al. |
| 6,592,599 B2 | 7/2003 | Vibe-Hansen et al. |
| 6,599,300 B2 | 7/2003 | Vibe-Hansen et al. |
| 6,599,301 B2 | 7/2003 | Vibe-Hansen et al. |
| 6,599,515 B1 | 7/2003 | Delmotte |
| 6,623,963 B1 | 9/2003 | Muller et al. |
| 6,626,950 B2 | 9/2003 | Brown et al. |
| 6,630,000 B1 | 10/2003 | Bonutti |
| 6,632,247 B2 | 10/2003 | Boyer, II et al. |
| 6,652,592 B1 | 11/2003 | Grooms et al. |
| 6,652,593 B2 | 11/2003 | Boyer, II et al. |
| 6,652,872 B2 | 11/2003 | Nevo et al. |
| 6,662,805 B2 | 12/2003 | Frondoza et al. |
| 6,666,892 B2 | 12/2003 | Hiles et al. |
| 6,686,184 B1 | 2/2004 | Anderson et al. |
| 6,687,747 B1 | 2/2004 | Filvaroff et al. |
| 6,689,747 B2 | 2/2004 | Filvaroff et al. |
| 6,696,073 B2 | 2/2004 | Boyce et al. |
| 6,712,851 B1 | 3/2004 | Lemperle et al. |
| 6,727,224 B1 | 4/2004 | Zhang et al. |
| 6,730,314 B2 | 5/2004 | Jeschke et al. |
| 6,734,018 B2 | 5/2004 | Wolfinbarger, Jr. et al. |
| 6,743,232 B2 | 6/2004 | Overaker et al. |
| 6,752,834 B2 | 6/2004 | Geistlich et al. |
| 6,761,739 B2 | 7/2004 | Shepard |
| 6,761,887 B1 | 7/2004 | Kavalkovich et al. |
| 6,767,369 B2 * | 7/2004 | Boyer et al. ............ 623/23.63 |
| 6,776,800 B2 | 8/2004 | Boyer, II et al. |
| 6,783,712 B2 | 8/2004 | Slivka et al. |
| 6,808,585 B2 | 10/2004 | Boyce et al. |
| 6,815,416 B2 | 11/2004 | Carney et al. |
| 6,838,440 B2 | 1/2005 | Stiles |
| 6,841,150 B2 | 1/2005 | Halvorsen et al. |
| 6,852,114 B2 | 2/2005 | Cerundolo |
| 6,852,125 B2 | 2/2005 | Simon et al. |
| 6,852,331 B2 | 2/2005 | Lai et al. |
| 6,855,167 B2 | 2/2005 | Shimp et al. |
| 6,855,169 B2 | 2/2005 | Boyer, II et al. |
| 6,858,042 B2 | 2/2005 | Nadler et al. |
| 6,866,668 B2 | 3/2005 | Giannetti et al. |
| 6,884,428 B2 | 4/2005 | Binette et al. |
| 6,890,354 B2 | 5/2005 | Steiner et al. |
| 6,893,462 B2 | 5/2005 | Buskirk et al. |
| 6,902,578 B1 | 6/2005 | Anderson et al. |
| 6,911,212 B2 | 6/2005 | Gertzman et al. |
| 6,932,977 B2 | 8/2005 | Heidaran et al. |
| 6,933,326 B1 | 8/2005 | Griffey et al. |
| 6,933,328 B2 | 8/2005 | Schacht |
| 6,949,252 B2 | 9/2005 | Mizuno et al. |
| 6,989,034 B2 | 1/2006 | Hammer et al. |
| 6,995,013 B2 | 2/2006 | Connelly et al. |
| 7,009,039 B2 | 3/2006 | Yayon et al. |
| 7,018,416 B2 | 3/2006 | Hanson et al. |
| 7,033,587 B2 | 4/2006 | Halvorsen et al. |
| 7,041,641 B2 | 5/2006 | Rueger et al. |
| 7,044,968 B1 | 5/2006 | Yaccarino, III et al. |
| 7,045,141 B2 | 5/2006 | Merboth et al. |
| 7,048,750 B2 | 5/2006 | Vibe-Hansen et al. |
| 7,048,762 B1 | 5/2006 | Sander et al. |
| 7,048,765 B1 | 5/2006 | Grooms et al. |
| 7,067,123 B2 | 6/2006 | Gomes et al. |
| 7,070,942 B2 | 7/2006 | Heidaran et al. |
| 7,078,232 B2 | 7/2006 | Konkle et al. |
| 7,108,721 B2 | 9/2006 | Huckle et al. |
| RE39,321 E | 10/2006 | MacPhee et al. |
| 7,115,146 B2 | 10/2006 | Boyer, II et al. |
| 7,125,423 B2 | 10/2006 | Hazebrouck |
| 7,132,110 B2 | 11/2006 | Kay et al. |
| 7,137,989 B2 | 11/2006 | Asculai et al. |
| 7,141,072 B2 | 11/2006 | Geistlich et al. |
| 7,156,880 B2 | 1/2007 | Evans et al. |
| 7,157,428 B2 | 1/2007 | Kusanagi et al. |
| 7,163,563 B2 | 1/2007 | Schwartz et al. |
| 7,166,133 B2 | 1/2007 | Evans et al. |
| 7,179,299 B2 | 2/2007 | Edwards et al. |
| 7,182,781 B1 | 2/2007 | Bianchi et al. |
| 7,201,917 B2 | 4/2007 | Malaviya et al. |
| 7,217,294 B2 | 5/2007 | Kusanagi et al. |
| 7,220,558 B2 | 5/2007 | Luyten et al. |
| 7,241,316 B2 | 7/2007 | Evans et al. |
| 7,252,987 B2 | 8/2007 | Bachalo et al. |
| 7,264,634 B2 | 9/2007 | Schmieding |
| 7,288,406 B2 | 10/2007 | Bogin et al. |
| 7,291,169 B2 | 11/2007 | Hodorek |
| 7,297,161 B2 | 11/2007 | Fell |
| 7,316,822 B2 | 1/2008 | Binette et al. |

| | | | | | |
|---|---|---|---|---|---|
| 7,323,011 B2 | 1/2008 | Shepard et al. | 2003/0229400 A1 | 12/2003 | Masuda et al. |
| 7,323,445 B2 | 1/2008 | Zhang et al. | 2003/0236573 A1* | 12/2003 | Evans et al. ............... 623/23.58 |
| 7,335,508 B2 | 2/2008 | Yayon et al. | 2004/0028717 A1 | 2/2004 | Sittinger et al. |
| 7,338,492 B2 | 3/2008 | Singhatat | 2004/0033212 A1 | 2/2004 | Thomson et al. |
| 7,338,524 B2 | 3/2008 | Fell et al. | 2004/0039447 A1 | 2/2004 | Simon et al. |
| 7,358,284 B2 | 4/2008 | Griffey et al. | 2004/0044408 A1 | 3/2004 | Hungerford et al. |
| 7,361,195 B2 | 4/2008 | Schwartz et al. | 2004/0062753 A1 | 4/2004 | Rezania et al. |
| 7,365,051 B2 | 4/2008 | Paulista et al. | 2004/0078090 A1 | 4/2004 | Binette et al. |
| 7,371,400 B2 | 5/2008 | Borenstein et al. | 2004/0102850 A1 | 5/2004 | Shepard |
| 7,468,075 B2 | 12/2008 | Lang et al. | 2004/0115172 A1 | 6/2004 | Bianchi et al. |
| 7,468,192 B2 | 12/2008 | Mizuno et al. | 2004/0134502 A1 | 7/2004 | Mizuno et al. |
| 7,479,160 B2 | 1/2009 | Branch et al. | 2004/0138748 A1 | 7/2004 | Boyer, II et al. |
| 7,485,310 B2 | 2/2009 | Luyten et al. | 2004/0143344 A1 | 7/2004 | Malaviya et al. |
| 7,488,348 B2 | 2/2009 | Truncale et al. | 2004/0151705 A1 | 8/2004 | Mizuno et al. |
| 7,513,910 B2 | 4/2009 | Buskirk et al. | 2004/0166169 A1 | 8/2004 | Malaviya et al. |
| 7,531,000 B2 | 5/2009 | Hodorek | 2004/0170610 A1 | 9/2004 | Slavin et al. |
| 7,537,617 B2 | 5/2009 | Bindsell et al. | 2004/0175826 A1 | 9/2004 | Maor |
| 7,537,780 B2 | 5/2009 | Mizuno et al. | 2004/0192605 A1 | 9/2004 | Zhang et al. |
| 7,550,007 B2 | 6/2009 | Malinin | 2004/0193268 A1 | 9/2004 | Hazebrouck |
| 7,563,455 B2 | 7/2009 | McKay | 2004/0197311 A1 | 10/2004 | Brekke et al. |
| 7,563,769 B2 | 7/2009 | Bogin et al. | 2004/0197373 A1 | 10/2004 | Gertzman et al. |
| 7,601,173 B2 | 10/2009 | Messerli et al. | 2004/0219182 A1 | 11/2004 | Gomes et al. |
| 7,608,113 B2 | 10/2009 | Boyer, II et al. | 2004/0220574 A1 | 11/2004 | Pelo et al. |
| 7,621,963 B2 | 11/2009 | Simon et al. | 2004/0230303 A1 | 11/2004 | Gomes et al. |
| 7,622,438 B1 | 11/2009 | Lazarov et al. | 2004/0243242 A1 | 12/2004 | Sybert et al. |
| 7,622,562 B2 | 11/2009 | Thorne et al. | 2005/0004672 A1 | 1/2005 | Pafford et al. |
| 7,628,851 B2 | 12/2009 | Armitage et al. | 2005/0027307 A1 | 2/2005 | Schwartz et al. |
| 7,632,311 B2 | 12/2009 | Seedhom et al. | 2005/0043814 A1 | 2/2005 | Kusanagi et al. |
| 7,638,486 B2 | 12/2009 | Lazarov et al. | 2005/0064042 A1 | 3/2005 | Vunjak-Novakovia et al. |
| 7,642,092 B2 | 1/2010 | Maor | 2005/0074476 A1 | 4/2005 | Gendler et al. |
| 7,648,700 B2 | 1/2010 | Vignery et al. | 2005/0074481 A1 | 4/2005 | Brekke et al. |
| 7,648,965 B2 | 1/2010 | Vignery et al. | 2005/0089544 A1 | 4/2005 | Khouri et al. |
| 7,658,768 B2 | 2/2010 | Miller et al. | 2005/0101957 A1 | 5/2005 | Buskirk et al. |
| 7,662,184 B2 | 2/2010 | Edwards et al. | 2005/0112761 A1 | 5/2005 | Halvorsen et al. |
| 7,666,230 B2 | 2/2010 | Orban et al. | 2005/0125077 A1 | 6/2005 | Harmon et al. |
| 2001/0005592 A1 | 6/2001 | Bhatnagar et al. | 2005/0129668 A1 | 6/2005 | Giannetti et al. |
| 2001/0006634 A1 | 7/2001 | Zaleske et al. | 2005/0152882 A1 | 7/2005 | Kizer et al. |
| 2001/0010023 A1 | 7/2001 | Schwartz et al. | 2005/0159820 A1 | 7/2005 | Yoshikawa et al. |
| 2001/0011131 A1 | 8/2001 | Luyten et al. | 2005/0159822 A1 | 7/2005 | Griffey et al. |
| 2001/0016646 A1 | 8/2001 | Rueger et al. | 2005/0196460 A1 | 9/2005 | Malinin |
| 2001/0018619 A1 | 8/2001 | Enzerink et al. | 2005/0222687 A1 | 10/2005 | Vunjak-Novakovia et al. |
| 2001/0020188 A1 | 9/2001 | Sander | 2005/0240281 A1 | 10/2005 | Slivka et al. |
| 2001/0021875 A1 | 9/2001 | Enzerink et al. | 2005/0251268 A1 | 11/2005 | Truncale |
| 2001/0031254 A1* | 10/2001 | Bianchi et al. ............... 424/93.7 | 2005/0260612 A1 | 11/2005 | Padmini et al. |
| 2001/0039457 A1* | 11/2001 | Boyer et al. ............... 623/23.52 | 2005/0261681 A9 | 11/2005 | Branch et al. |
| 2001/0039458 A1 | 11/2001 | Boyer, II et al. | 2005/0261767 A1 | 11/2005 | Anderson et al. |
| 2001/0043940 A1 | 11/2001 | Boyce et al. | 2005/0288796 A1 | 12/2005 | Awad et al. |
| 2001/0051834 A1 | 12/2001 | Frondoza et al. | 2006/0030948 A1 | 2/2006 | Manrique et al. |
| 2002/0009805 A1 | 1/2002 | Nevo et al. | 2006/0060209 A1 | 3/2006 | Shepard |
| 2002/0016592 A1 | 2/2002 | Branch et al. | 2006/0099234 A1 | 5/2006 | Winkler |
| 2002/0035401 A1 | 3/2002 | Boyce et al. | 2006/0111778 A1 | 5/2006 | Michalow |
| 2002/0042373 A1 | 4/2002 | Carney et al. | 2006/0167483 A1 | 7/2006 | Asculai et al. |
| 2002/0045940 A1 | 4/2002 | Giannetti et al. | 2006/0178748 A1 | 8/2006 | Dinger, II et al. |
| 2002/0055783 A1 | 5/2002 | Tallarida et al. | 2006/0200166 A1 | 9/2006 | Hanson et al. |
| 2002/0072806 A1 | 6/2002 | Buskirk et al. | 2006/0210643 A1 | 9/2006 | Truncale et al. |
| 2002/0082704 A1 | 6/2002 | Cerundolo | 2006/0216323 A1 | 9/2006 | Knaack et al. |
| 2002/0099448 A1 | 7/2002 | Hiles et al. | 2006/0216822 A1 | 9/2006 | Mizuno et al. |
| 2002/0106393 A1 | 8/2002 | Bianchi et al. | 2006/0235534 A1 | 10/2006 | Gertzman et al. |
| 2002/0111695 A1 | 8/2002 | Kandel | 2006/0247790 A1 | 11/2006 | McKay |
| 2002/0120274 A1 | 8/2002 | Overaker et al. | 2006/0247791 A1 | 11/2006 | McKay et al. |
| 2002/0138143 A1 | 9/2002 | Grooms et al. | 2006/0251631 A1 | 11/2006 | Adkisson, IV et al. |
| 2002/0177224 A1 | 11/2002 | Madry et al. | 2006/0276907 A1 | 12/2006 | Boyer, II et al. |
| 2002/0192263 A1 | 12/2002 | Merboth et al. | 2007/0009610 A1 | 1/2007 | Syring |
| 2003/0021827 A1 | 1/2003 | Malaviya et al. | 2007/0014867 A1 | 1/2007 | Kusanagi et al. |
| 2003/0023316 A1 | 1/2003 | Brown et al. | 2007/0026030 A1 | 2/2007 | Gill et al. |
| 2003/0032961 A1 | 2/2003 | Pelo et al. | 2007/0036834 A1 | 2/2007 | Pauletti et al. |
| 2003/0033021 A1 | 2/2003 | Plouhar et al. | 2007/0041950 A1 | 2/2007 | Leatherbury et al. |
| 2003/0033022 A1 | 2/2003 | Plouhar et al. | 2007/0055377 A1 | 3/2007 | Hanson et al. |
| 2003/0036797 A1 | 2/2003 | Malaviya et al. | 2007/0065943 A1 | 3/2007 | Smith et al. |
| 2003/0036801 A1* | 2/2003 | Schwartz et al. .......... 623/23.63 | 2007/0067032 A1 | 3/2007 | Felt et al. |
| 2003/0039695 A1 | 2/2003 | Geistlich et al. | 2007/0083266 A1 | 4/2007 | Lang |
| 2003/0040113 A1 | 2/2003 | Mizuno et al. | 2007/0093896 A1 | 4/2007 | Malinin |
| 2003/0044444 A1 | 3/2003 | Malaviya et al. | 2007/0093912 A1 | 4/2007 | Borden |
| 2003/0049299 A1 | 3/2003 | Malaviya et al. | 2007/0098759 A1 | 5/2007 | Malinin |
| 2003/0050709 A1 | 3/2003 | Noth et al. | 2007/0100450 A1 | 5/2007 | Hodorek |
| 2003/0055502 A1 | 3/2003 | Lang et al. | 2007/0113951 A1 | 5/2007 | Huang |
| 2003/0078617 A1 | 4/2003 | Schwartz et al. | 2007/0128155 A1 | 6/2007 | Seyedin |
| 2003/0099620 A1 | 5/2003 | Zaleske et al. | 2007/0134291 A1 | 6/2007 | Ting |
| 2003/0144743 A1 | 7/2003 | Edwards et al. | 2007/0135917 A1 | 6/2007 | Malinin |

| | | | |
|---|---|---|---|
| 2007/0135918 A1 | 6/2007 | Malinin | |
| 2007/0135928 A1 | 6/2007 | Malinin | |
| 2007/0148242 A1 | 6/2007 | Vilei et al. | |
| 2007/0162121 A1 | 7/2007 | Tarrant et al. | |
| 2007/0168030 A1 | 7/2007 | Edwards et al. | |
| 2007/0172506 A1 | 7/2007 | Nycz et al. | |
| 2007/0179607 A1 | 8/2007 | Hodorek et al. | |
| 2007/0185585 A1 | 8/2007 | Bracy et al. | |
| 2007/0276506 A1 | 11/2007 | Troxel | |
| 2007/0299517 A1 | 12/2007 | Davisson et al. | |
| 2007/0299519 A1 | 12/2007 | Schmieding | |
| 2008/0015709 A1 | 1/2008 | Evans et al. | |
| 2008/0027546 A1 | 1/2008 | Semler et al. | |
| 2008/0031915 A1 | 2/2008 | Becerra Ratia et al. | |
| 2008/0038314 A1 | 2/2008 | Hunziker | |
| 2008/0039939 A1 | 2/2008 | Iwamoto et al. | |
| 2008/0039954 A1 | 2/2008 | Long et al. | |
| 2008/0039955 A1 | 2/2008 | Hunziker | |
| 2008/0051889 A1 | 2/2008 | Hodorek | |
| 2008/0065210 A1 | 3/2008 | McKay | |
| 2008/0077251 A1 | 3/2008 | Chen et al. | |
| 2008/0119947 A1 | 5/2008 | Huckle et al. | |
| 2008/0125863 A1 | 5/2008 | McKay | |
| 2008/0125868 A1 | 5/2008 | Branemark | |
| 2008/0138414 A1 | 6/2008 | Huckle et al. | |
| 2008/0153157 A1 | 6/2008 | Yao et al. | |
| 2008/0154372 A1 | 6/2008 | Peckham | |
| 2008/0167716 A1 | 7/2008 | Schwartz et al. | |
| 2008/0183300 A1 | 7/2008 | Seedhom et al. | |
| 2008/0274157 A1 | 11/2008 | Vunjak-Novakovic et al. | |
| 2008/0305145 A1 | 12/2008 | Shelby et al. | |
| 2009/0069901 A1 | 3/2009 | Truncale et al. | |
| 2009/0069904 A1 | 3/2009 | Picha | |
| 2009/0076624 A1 | 3/2009 | Rahaman et al. | |
| 2009/0099661 A1 | 4/2009 | Bhattacharya et al. | |
| 2009/0117652 A1 | 5/2009 | Luyten et al. | |
| 2009/0131986 A1 | 5/2009 | Lee et al. | |
| 2009/0210057 A1 | 8/2009 | Liao et al. | |
| 2009/0226523 A1 | 9/2009 | Behnam et al. | |
| 2009/0280179 A1 | 11/2009 | Neumann et al. | |
| 2009/0299475 A1 | 12/2009 | Yamamoto et al. | |
| 2009/0312805 A1 | 12/2009 | Lang et al. | |
| 2009/0312842 A1 | 12/2009 | Bursac et al. | |
| 2009/0319051 A9 | 12/2009 | Nycz et al. | |
| 2010/0021521 A1 | 1/2010 | Xu et al. | |
| 2010/0036492 A1 | 2/2010 | Hung et al. | |
| 2010/0036503 A1 | 2/2010 | Chen et al. | |

FOREIGN PATENT DOCUMENTS

| | | | |
|---|---|---|---|
| EP | 0522569 A1 | 1/1993 | |
| EP | 0762903 B1 | 6/1995 | |
| EP | 0762903 A1 | 12/1995 | |
| EP | 0517030 B1 | 9/1996 | |
| EP | 0739631 A2 | 10/1996 | |
| EP | 0784985 A1 | 7/1997 | |
| EP | 0968012 A1 | 9/1998 | |
| EP | 1719531 A2 | 5/2001 | |
| EP | 1237511 A1 | 6/2001 | |
| EP | 1237511 B1 | 6/2001 | |
| EP | 1127581 A1 | 8/2001 | |
| EP | 1181908 A1 | 2/2002 | |
| EP | 1234552 A1 | 8/2002 | |
| EP | 1234555 A2 | 8/2002 | |
| EP | 0762903 B1 | 9/2003 | |
| EP | 0739631 B1 | 12/2003 | |
| EP | 1181908 B1 | 12/2003 | |
| EP | 1384452 A1 | 1/2004 | |
| EP | 1234555 A3 | 6/2004 | |
| EP | 1237511 B1 | 9/2004 | |
| EP | 1618178 A1 | 11/2004 | |
| EP | 1127581 B1 | 6/2005 | |
| EP | 1561481 A2 | 8/2005 | |
| EP | 1618178 B1 | 1/2006 | |
| EP | 1234552 B1 | 8/2006 | |
| EP | 0968012 B1 | 9/2006 | |
| EP | 1719463 A1 | 11/2006 | |
| EP | 1719531 A2 | 11/2006 | |
| EP | 1719532 A2 | 11/2006 | |
| EP | 1234555 B1 | 2/2007 | |
| EP | 0762903 B2 | 8/2007 | |
| EP | 1537863 B1 | 4/2008 | |
| GB | 2102811 A1 | 2/1983 | |
| SU | 1454423 A1 | 1/1989 | |
| WO | WO 84/04880 A1 | 12/1984 | |
| WO | 90/001342 A1 | 2/1990 | |
| WO | 93/016739 A1 | 9/1993 | |
| WO | WO 94/03584 A1 | 2/1994 | |
| WO | 95/025748 A1 | 9/1995 | |
| WO | WO 95/33502 A1 | 12/1995 | |
| WO | 96/024310 A1 | 8/1996 | |
| WO | WO 98/14222 A1 | 4/1998 | |
| WO | WO 98/41246 A2 | 9/1998 | |
| WO | 98-043686 A1 | 10/1998 | |
| WO | WO 99/09914 A1 | 3/1999 | |
| WO | WO 99/11298 A2 | 3/1999 | |
| WO | WO 99/21497 | * 5/1999 | |
| WO | WO 99/22747 A1 | 5/1999 | |
| WO | WO 99/48541 A1 | 9/1999 | |
| WO | WO 99/52572 A1 | 10/1999 | |
| WO | 99/015209 A1 | 11/1999 | |
| WO | 99/056797 A1 | 11/1999 | |
| WO | WO 00/40177 A1 | 7/2000 | |
| WO | 00/047114 A1 | 8/2000 | |
| WO | 01/007595 A2 | 2/2001 | |
| WO | 01/038357 A2 | 5/2001 | |
| WO | 01/039788 A2 | 6/2001 | |
| WO | 01/046416 A1 | 6/2001 | |
| WO | WO 01/43667 A1 | 6/2001 | |
| WO | 02/018546 A2 | 3/2002 | |
| WO | 02/022779 A2 | 3/2002 | |
| WO | 02/036732 A2 | 5/2002 | |
| WO | WO 02/058484 A2 | 8/2002 | |
| WO | WO 02/064180 A1 | 8/2002 | |
| WO | 04/077199 A2 | 10/2002 | |
| WO | 02/095019 A1 | 11/2002 | |
| WO | 03/007873 A2 | 1/2003 | |
| WO | WO 03/007805 A2 | 1/2003 | |
| WO | WO 03/007805 A3 | 1/2003 | |
| WO | WO 03/007879 A2 | 1/2003 | |
| WO | 2003/012053 A2 | 2/2003 | |
| WO | WO 03/007879 A3 | 8/2003 | |
| WO | 03/079985 A2 | 10/2003 | |
| WO | 03/087160 A1 | 10/2003 | |
| WO | 03/094835 A2 | 11/2003 | |
| WO | WO 03/007805 A3 | 2/2004 | |
| WO | 04/067704 A2 | 8/2004 | |
| WO | 04/069298 A1 | 8/2004 | |
| WO | 2004/067704 A2 | 8/2004 | |
| WO | WO 2004/075940 A1 | 9/2004 | |
| WO | WO 2004/096983 A2 | 11/2004 | |
| WO | WO 2004/096983 A3 | 11/2004 | |
| WO | WO 2004/103224 A1 | 12/2004 | |
| WO | 2005058207 A1 | 6/2005 | |
| WO | WO 2005/110278 A2 | 11/2005 | |
| WO | WO 2005/110278 A3 | 11/2005 | |
| WO | WO 2004/096983 A3 | 12/2005 | |
| WO | WO 2006/042311 A2 | 4/2006 | |
| WO | WO 2006/042311 A3 | 4/2006 | |
| WO | 2006/050213 A2 | 5/2006 | |
| WO | WO 2005/110278 A3 | 8/2006 | |
| WO | 2002/036732 A3 | 9/2006 | |
| WO | 2006/113586 A2 | 10/2006 | |
| WO | WO 2006/042311 A3 | 11/2006 | |
| WO | 03/094835 A3 | 12/2006 | |
| WO | WO 2007/024238 A1 | 3/2007 | |
| WO | 2006/113586 A3 | 9/2007 | |
| WO | 2008/013763 A2 | 1/2008 | |
| WO | WO 2008/021127 A2 | 2/2008 | |
| WO | 2008/038287 A2 | 4/2008 | |
| WO | 2008/013763 A3 | 6/2008 | |
| WO | 2008/081463 A2 | 7/2008 | |
| WO | 2008/038287 A3 | 9/2008 | |
| WO | WO 2008/106254 A2 | 9/2008 | |
| WO | WO 2009/076164 A2 | 6/2009 | |
| WO | WO 2009/111069 A1 | 9/2009 | |

OTHER PUBLICATIONS

Bugbee, William D., Fresh Osteochondral Allografting, Operative

Techniques in Sports Medicine, Apr. 2000, vol. 8, No. 2; pp. 158-162.*

Nettles et al., "In Situ Crosslinkable Hyaluronan For Articular Cartilage Repair", 50th Annual Meeting of the Orthopaedic Research Society, Paper No. 2020.

Nettles et al., "Photocrosslinkable Hyaluronan As a Scaffold for Articular Cartilage Repair", Annals of Biomedical Engineering, vol. 32, No. 3, Mar. 2004, pp. 391-397.

Verbruggen et al., "Repair Function in Organ Cultured Human Cartilage. Replacement fo Enzymatically Removed Proteoglycans During Longterm Organ Culture", The Journal of Rheumatology, 12:4, (1985), pp. 665-674.

Chen et al., "Repair of Articular Cartilage Defects: Part 1. Basic Science of Cartilage Healing", The American Journal of Orthopaedics (Jan. 1999) pp. 31-33.

Jackson et al., "Cartilage Substitute: Overview of Basic Science & Treatment Options", Journal of American Academy of Orthopaedic Surgeons, vol. 9 (Jan./Feb. 2001) pp. 37-52.

Peretti et al., "Cell-Based Bonding of Articular Cartilage: An Extended Study", Wiley Publications, Inc., 2003 pp. 517-524.

Hunziker, "Articular Cartilage Repair: Basic Science and Clinical Progress. A Review of the Current Status and Prospects", Osteoarthritis and Cartilage 2001, vol. 10, No. 6, pp. 432-463.

Chen et al., "Repair of Articular Cartilage Defects: Part II. Treatment Options", The American Journal of Orthopedics, Feb. 1999, pp. 88-96.

Buckwalter, "Articular Cartilage Injuries", Clinical Orthopaedics and Related Research, 2002, No. 402, pp. 21-37.

Nixon et al., "New Horizons in Articular Cartilage Repair", Proceedings of the Annual Convention of the AAEP, 2001, vol. 47, pp. 217-226.

Tsumaki et al. "Role of CDMP-1 in Skeletal Morphogenesis: Promotion of Mesenchymal Cell Recruitment and Chondrocyte Differentiation", J. Cell Biol., Jan. 1999, vol. 144, No. 1, 161-173.

Glowacki, "Engineered Cartilage, Bone, Joints and Menisci-Potential for Temporomandibular Joint Reconstruction", Cells tissues Organs, vol. 169, Issue 3, 2001, pp. 302-308.

Peretti et al., "A Biomechanical Analysis of an Engineered Cell-Scaffold Implant for Cartilage Repair", Annals of Plastic Surgery, 2001, vol. 46, No. 5, pp. 533-537.

Peretti et al., "Biomechanical Analysis of a Chondrocyte-Based Repair Model of Articular Cartilage", Tissue Engineering, Aug. 1, 1999, vol. 5, No. 4, pp. 317-326.

Peretti et al., "In Vitro Bonding of Pre-seeded Chondrocytes", Sport Sciences for Health, May 1, 2007, vol. 2, No. 1, pp. 29-33.

Peretti et al., "Bonding of Cartilage Matrices with Cultured Chondrocytes: An Experimental Model", Journal of Orthopedic Research, Jan. 1998, vol. 16, No. 1, pp. 89-95.

Trzeciak et al., "Evaluation of Cartilage Reconstruction by Means of Autologous Chondrocyte Versus Periosteal Graft Transplantation: An Animal Study", Transplantation Proceedings, vol. 38 (2006), pp. 305-311.

Brighton et al., "Articular Cartilage Preservation and Storage—I. Application of Tissue Culture Techniques to the Storage of Viable Articular Cartilage", Arthritis and Rheumatism, vol. 22, No. 10 (Oct. 1979), pp. 1093-1101.

Mahadev et al., "Autogenous Osteochondral Morselised Grafts for Full Thickness Osteochondral Defects in the Knee Joints of Pigs", Singapore Medical Journal, 2001, vol. 42(9), pp. 410-416.

Hunziker, "Articular Cartilage Structure in Humans and Experimental Animals", *Articular Cartilage and Osteoarthritis*, Raven Press, ed., 2001, pp. 183-199.

Girotto et al., "Tissue-specific gene expression in chondrocytes grown on three-dimensional hyaluronic acid scaffolds", Biomaterials, vol. 24 (2003), pp. 3265-3275.

Gertzman et al., "A pilot study evaluating sodium hyaluronate as a carrier for freeze-dried demineralized bone powder", Cell and Tissue Banking, vol. 2, 2001, pp. 87-94.

Non-final Office Action mailed on Apr. 19, 2007 in connection with U.S. Appl. No. 11/151,270.

Final Office Action mailed on Oct. 9, 2007 in connection with U.S. Appl. No. 11/151,270.

Advisory Action mailed on Dec. 27, 2007 in connection with U.S. Appl. No. 11/151,270.

Office Action mailed Feb. 7, 2008 in conneciton with U.S. Appl. No. 10/815,778.

Non-final Office Action mailed on Feb. 20, 2007 in connection with U.S. Appl. No. 10/960,960.

Final Office Action mailed on Sep. 28, 2007 in connection with U.S. Appl. No. 10/960,960.

U.S. Appl. No. 12/010,984, filed Jan. 31, 2008 titled Cartilage Repair Mixture Containing Allograft Chondroctyes.

U.S. Appl. No. 11/657,042, filed Jan. 24, 2007 titled Two Piece Cancellous Construct for Cartilage Repair.

U.S. Appl. No. 12/043,001, filed Mar. 5, 2008 titled Cancellous Construct With Support Ring for Repair of Osteochondral Defects.

International Search Report issued in connection with International Patent Application No. PCT/US2004/010957 on Nov. 1, 2004.

Written Opinion issued on Nov. 1, 2004 in connection with International Patent Application No. PCT/US2004/010957.

International Preliminary Report on Patentability issued on Nov. 18, 2005 in connection with International Patent Application No. PCT/US2004/010957.

Written Opinion issued on Apr. 7, 2006 in connection with International Patent Applicaiton No. PCT/US2005/030610.

International Preliminary Report on Patentability issued on Feb. 26, 2008 in connection with International Patent Application No. PCT/US2005/030610.

International Search Report issued in connection with International Patent Application No. PCT/US2005/030610 on Apr. 7, 2006.

International Search Report issued in connection with International Patent Application No. PCT/US2005/036878 on Sep. 21, 2006.

Written Opinion issued on Sep. 21, 2006 in connection with International Patent Application No. PCT/US2005/036878.

International Preliminary Report on Patentability issued on Apr. 17, 2007 2006 in connection with International Patent Application No. PCT/US2005/036878.

International Search Report issued in connection with International Application No. PCT/US2005/008798 on Jun. 19, 2006.

International Search Report issued in connection with International Application PCT/US2004/010956 on Oct. 28, 2005.

International Patent Application No. PCT/US2008/051796 filed Jan. 23, 2008 titled Two Piece Cancellous Construct for Cartilage Repair.

Diduch et al., "Joint Repair: Treatment Options for Articular Cartilage Injury", Orthopedic Technology Review 2002: 4:24-27.

Stone et al., "One-Step American Technique of Articular Cartilage Paste Grafting to Traumatic and Arthritic Defects in the Knee Joint (2-7 Years Follow Up)", downloaded from http://www.stoneclinic.com/onestep.htm, publication date unknown.

Hunziker, "Articular Cartilage Structure in Humans and Experimental Animals", *Articular Cartilage and Osteoarthritis*, Raven Press, ed., 1992, pp. 183-199.

U.S. Appl. No. 12/079,629, filed Mar. 26, 2008 titled Cartilage Implant Plug With Fibrin Glue and Method for Implantation.

Feczkó et al., "Experimental Results of Donor Site Filling for Autologous Osteochondral Mosaicplasty", Arthroscopy: The J. Arthroscopic and Related Surg., vol. 19 No. 7 (Sep. 2003) pp. 755-761.

Peretti et al., "Cell-Based Tissue-Engineered Allogeneic Implant for Cartilage Repair", Tissue Engineering (Oct. 2000), pp. 567-576, vol. 6, No. 5, Mary Ann Liebert, Inc.

Hoffman, "Hydrogels for Biomedical Applications", Advanced Drug Delivery Reviews, 2002, vol. 43, pp. 3-12.

Dahlberg et al., "Demineralized Allogeneic Bone Matrix for Cartilage Repair", Journal of Orthopaedic Research, 1991, vol. 9, pp. 11-19.

Lu et al., "Minced Cartilage without Cell Culture Serves as an Effective Intraoperative Cell Source for Cartilage Repair", Journal of Orthopaedic Research, Jun. 2006, vol. 24, pp. 1261-1270.

Stone et al., "Articular Cartilage Paste Grafting to Full-Thickness Articular Cartilage Knee Joint Lesions: A 2- to 12-Year Follow-up", Arthroscopy: The Journal of Arthroscopic and Related Surgery, Mar. 2006, vol. 22, No. 3, pp. 291-299.

Newman, "Articular Cartilage Repair", American Journal of Sports Medicine, 1998, vol. 26, No. 2, pp. 309-324.

Brittberg et al., "Treatment of Deep Cartilage Defects in the Knee with Autologous Chondrocyte Transplantation", New England Journal of Medicine, Oct. 6, 1994, vol. 331, No. 14 pp. 889-895.

Nixon et al., "Enhanced Repair of Extensive Articular Defects by Insulin-like Growth Factor-I-Laden Fibrin Composites", Journal of Orthopaedic Research, 1999; 17:475-487.

International Cartilage Repair Society, "Cartilage Injury Evaluation Package", www.cartilage.org, 2000.

Richardson et al., "Repair of Human Articular Cartilage After Implantation of Autologous Chondrocytes", Journal of Bone and Joint Surgery [Br], 1999; 81-B:1064-1068.

Brittberg et al., "Autologous Chondrocytes Used for Articular Cartilage Repair: An Update", Clinical Orthopaedics and Related Research, 2001; No. 391 Suppl: S337-S348.

Peterson et al., "Two- to 9-year Outcome After Autologous Chondrocyte Transplantation of the Knee", Clinical Orthopaedics and Related Research, 2000; No. 374: 212-234.

Peterson et al., "Autologous Chondrocyte Transplantation: Biomechanics and Long-term Durability", American Journal of Sports Medicine, 2002, vol. 30, No. 1, pp. 2-12.

Messner et al., "Cartilage Repair: A Critical Review", Acta Orthopaedica Scandinavica, 1996, vol. 67, No. 5, pp. 523-529.

Messner et al., "The long-term Prognosis for Severe Damage to Weight-bearing Cartilage in the Knee: A 14-year Clinical and Radiographic Follow-up in 28 Young Athletes", Acta Orthopaedica Scandinavica, 1996, vol. 67, No. 2, pp. 165-168.

Buckwalter et al., "Articular Cartilage: Degeneration and Osteoarthritis, Repair, Regeneration, and Transplantation", AAOS Instructional Course Lectures, 1998; 47:487-504.

Breinan et al., "Effect of Cultured Autologous Chondrocytes on Repair of Chondral Defects in a Canine Model", Journal of Bone and Joint Surgery [Am], 1997; 79-A:1439-1451.

Breinan et al., "Autologous Chondrocyte Implantation in a Canine Model: Change in Composition of Reparative Tissue with Time", Journal of Orthopaedic Research, 2001; 19:482-492.

Brittberg et al., "Rabbit Articular Cartilage Defects Treated with Autologous Cultured Chondrocytes", Clinical Orthopaedics and Related Research, 1996; 326:270-283.

Nehrer et al., "Chondrocyte-seeded Collagen Matrices Implanted in a Chondral Defect in a Canine Model", Biomaterials, 1998; 19:2313-2328.

Vunjak-Novakovic et al., "Bioreactor Cultivation Conditions Modulate the Composition and Mechanical Properties of Tissue-Engineered Cartilage", Journal of Orthopaedic Research, 1999; 17:130-138.

Bursac, "Collagen Network Contributions to Structure-Function Relationships in Cartilaginous Tissues in Compression" (Dissertation), Boston University College of Engineering, 2002.

Gooch et al., "IGF-I and Mechanical Environment Interact to Modulate Engineered Cartilage Development", Biochemical and Biophysical Research Communications, 2001; 286:909-915.

Pei et al., "Growth Factors for Sequential Cellular De- and Re-differentiation in Tissue Engineering", Biochemical and Biophysical Research Communicaitons, 2002; 294:149-154.

Obradovic et al., "Integration of Engineered Cartilage", Journal of Orthopaedic Research, 19 (6):1089-1097, 2001.

Schaefer et al., "Tissue Engineered Composites for the Repair of Large Osteochondral Defects", Arthritis & Rheumatism, 46(9): 2524-2534 (2002).

Pei et al., "Bioreactors Mediate the Effectiveness of Tissue Engineering Scaffolds", the FASEB Journal, 16:1691-1694, published online (Aug. 7, 2002), 10.1096/fj.02-0083fje.

Madry et al., "Gene Transfer of a Human Insulin-like Growth Factor I cDNA Enhances Tissue Engineering of Cartilage", Human Gene Therapy, 13: 1621-1630 (Sep. 1, 2002).

Pearson et al. ( eds.), American Association of Tissue Banks, Standards for Tissue Banking, 2008 (12th ed.), pp. 53-56, 86-88.

U.S. Appl. No. 12/147,042, filed Jun. 28, 2008 for Glue for Cartilage Repair.

U.S. Appl. No. 12/191,490, filed Aug. 14, 2008 for Cartilage Implant Plug With Fibrin Glue and Method for Implantation.

U.S. Appl. No. 12/328,306, filed Dec. 4, 2008 for Cancellous Bone Implant for Cartilage Repair.

International. Patent Application No. PCT/US08/85522 filed Dec. 4, 2008 for Cancellous Bone Implant for Cartilage Repair.

U.S. Appl. No. 12/322,996, filed Feb. 9, 2009 for Allograft Osteochondral Plug Combined With Cartilage Particle Mixture.

U.S. Appl. No. 12/381,072, filed Mar. 5, 2009 for Cancellous Constructs, Cartilage Particles and Combinations of Cancellous Constructs and Cartilage Particles.

A final Office Action mailed on Nov. 13, 2008 in connection with U.S. Appl. No. 10/815,778.

Internatioinal. Patent Application No. PCT/US09/ 001459 filed Mar. 5, 2009 for Cancellous Constructs, Cartilage Particles and Combinations of Cancellous Constructs and Cartilage Particles.

A final Office Action mailed on Sep. 19, 2008 in connection with U.S. Appl. No. 11/081,103.

Osteo Sponge product information, Bacterin International Inc., May 2005.

Nolan et al., "Living Bone Grafts", BMJ, vol. 304, Jun. 13, 1992, pp. 1520 and 1521.

Stone et al., One-Step American Technique of Articular Cartilage Paste Grafting to Traumatic and Arthritic Defects in the Knee Joint (2-7 Years Follow-Up), downloaded from http:web.archive.org/web/20041205005845/http://www.stoneclinic.com/onestep.thm; published Dec. 5, 2004.

"Lyophilization" TechnoBusiness-Solutions, from URL: <http://www technobusiness-solutions.com/article-lyophilization1.html> 10 pages, published Feb. 12, 2002.

Non-final Office Action issued on Aug. 19, 2009 in connection with U.S. Appl. No. 12/147,042.

Non-final Office Action issued on Jul. 2, 2009 in connection with U.S. Appl. No. 10/815,778.

Non-final Office Action issued on May 18, 2009 in connection with U.S. Appl. No. 11/657,042.

Non-final Office Action issued on Jun. 3, 2009 in connection with U.S. Appl. No. 11/081,103.

Non-final Office Action issued on Jun. 8, 2009 in connection with U.S. Appl. No. 11/481,955.

Non-final Office Action issued on Jul. 22, 2009 in connection with U.S. Appl. No. 12/010,984.

Ornitz et al., "Protein Family Review: Fibroblast Growth Factors", Genome Biology (2001) 2(3): reviews 3005.1-3005.12, http://genomebiology.com/2001/2/3/reviews/3005.1.

Loeser et al., "Basic Fibroblast Growth Factor Inhibits the Anabolic Activity of Insulin-like Growth Factor 1 and Osteogenic Protein 1 in Adult Human Articular Chondrocytes", Arthritis & Rheumatism, vol. 52, No. 12 (Dec. 2005), pp. 3910-3917.

Kato et al., "Fibroblast Growth Factor is an Inhibitor of Chondrocyte Terminal Differentiation", Journal of Biological Chemistry, vol. 265, No. 10 (Apr. 5, 1990) pp. 5903-5909.

Andrés et al., "A Pro-Inflammatory Signature Mediates FGF2-induced Angiogenesis", Journal of Cellular and Molecular Medicine, (Jun. 28, 2008), available at http://www.ncbi.nlm.nih.gov/pubmed/18624773.

Burger et al., "Fibroblast growth factor receptor-1 is expressed by endothelial progenitor cells", Blood, vol. 100, No. 10 (Nov. 15, 2002) 3527-35.

Baird, "Fibroblast growth factors: activities and significance of non-neurotrophin neurotrophic growth factors", Current Opinions in Neurobiology, (1994) 4:78-86.

Mazué et al., "Preclinical and Clinical Studies with Recombinant Human Basic Fibroblast Growth Factor", Annals New York Academy of Sciences, (1991) 329-340.

Aviles et al., "Testing clinical therapeutic angiogenesis using basic fibroblast growth factor (FGF-2)", British Journal of Pharmacology (2003) 140: 637-646.

Gilbert, et al., "Decellularization of Tissues and Organs", Biomaterials (2006) 27:3675-3683.

http://www.stoneclinic.com/articularcartilagepastegrafting (Copyright 2009).

Non-final Office Action mailed on Jul. 9, 2008 in connection with U.S. Appl. No. 11/151,270.

Non-final Office Action mailed on Dec. 18, 2007 in connection with U.S. Appl. No. 11/081,103.

Non-final Office Action mailed on Oct. 5, 2005 in connection with U.S. Appl. No. 10/424,765.
U.S. Appl. No. 12/508,892 filed Jul. 24, 2009 entitled "Cancellous Construct With Support Ring for Repair of Osteochondral Defects".
Written Opinion issued on Jun. 19, 2006 in connection with International Patent Application No. PCT/US2005/0008798.
International Preliminary Report on Patentability issued on Nov. 1, 2006 in connection with International Patent Application No. PCT/US2005/0008798.
Written Opinion issued on Oct. 28, 2005 in connection with International Patent Application No. PCT/US2004/010956.
International Preliminary Report on Patentability issued on Nov. 18, 2005 in connection with International Patent Application No. PCT/US2004/010956.
International Search Report issued on Jun. 23, 2009 in connection with International Patent Application No. PCT/US2008/051796.
Written Opinion issued on Jun. 23, 2009 in connection with International Patent Application No. PCT/US2008/051796.
International Preliminary Report on Patentability issued on Jul. 28, 2009 in connection with International Patent Application No. PCT/US2008/051796.
International Search Report issued on Jul. 6, 2009 in connection with International Patent Application No. PCT/US2008/085522.
Written Opinion issued on Jul. 6, 2009 in connection with International Patent Application No. PCT/US2008/085522.
International Search Report issued on Jul. 6, 2009 in connection with International Patent Application No. PCT/US2009/001459.
Written Opinion issued on Jul. 6, 2009 in connection with International Patent Application No. PCT/US2009/001459.
Crescenzi et al., "Hyaluronan Linear and Crosslinked Derivatives as Potential/Actual Biomaterials", in Hyaluronan (2002), vol. 1 (Chemical, Biochemical and Biological Aspects), J. F. Kennedy et al., Ed., pp. 261-268.
Michielen et al., "Novel Biomaterials Based on Cross-linked Hyaluronan: Structural Investigations", in Hyaluronan (2002), vol. 1 (Chemical, Biochemical and Biological Aspects), J. F. Kennedy et al., Ed., pp. 269-276.
U.S. Appl. No. 12/657,207, filed Jan. 14, 2010, entitled "Cartilage Particle Tissue Mixtures Optionally Combined With a Cancellous Construct".
International Patent Application No. PCT/US2009/000108, filed Jan. 14, 2010, entitled "Cartilage Particle Tissue Mixtures Optionally Combined With a Cancellous Construct".
Final Office Action for U.S. Appl. No. 10/815,778, mailed Mar. 15, 2010.
Final Office Action for U.S. Appl. No. 12/010,984, mailed Mar. 22, 2010.
U.S. Appl. No. 12/696,366, filed Jan. 29, 2010, entitled "Engineered Osteochondral Construct for Treatment of Articular Cartilage Defects".
Non-Final Office Action for U.S. Appl. No. 11/081,103, mailed Jan. 14, 2010.
Final Office Action for U.S. Appl. No. 11/481,955, mailed Jan. 7, 2010.
Aston et al., "Repair of Articular Surfaces by Allografts of Articular and Growth-Plate Cartilage," Journal of Bone and Joint Surgery, Jan. 1986, vol. 68-B, No. 1; pp. 29-35.
Final Office Action for U.S. Appl. No. 11/657,042, mailed Dec. 28, 2009.
Non-Final Office Action for U.S. Appl. No. 11/657,042, mailed Apr. 15, 2010.
Non-Final Office Action for U.S. Appl. No. 12/079,629, mailed Apr. 15, 2010.
Non-Final Office Action for U.S. Appl. No. 12/191,490, mailed Apr. 12, 2010.
Abraham, Judith A. et al., (1986) Human Basic Fibroblast Growth Factor: Nucleotide Sequence and Genomic Organization. EMBO Journal 5(10):2523-2528.
Agrawal, Sudhir et al., (1991) Pharmacokinetics. Biodistribution, And Stability Of Oligodeoxynucleotide Phosphorothioates In Mice. Proc Natl Acad Sci. USA 88(17):7595-7599.

Arakawa, Tsutomu et al., (1993) Production and Characterization of an Analog of Acidic Fibroblast Growth Factor With Enhanced Stability and Biological Activity. Protein Engineering 6(5):541-546.
Bailly, Karine et al., (2000) Uncoupling of cell proliferation and differentiation activities of basic fibroblast growth factor. FASEB Journal 14(2):333-343.
Bange, Johannes et al., (2002) Cancer progression and tumor cell motility are associated with the FGFR4 Arg388 allele. Cancer Research 62(3):840-846.
Bork, Peer (2000) Powers and pitfalls in sequence analysis: The 70% hurdle. Genome Res. 10(4):398-400.
Bork, Peer and Bairoch, Amnon (1996) Go hunting in sequence databases but watch out for the traps. Trends in Genetics 12(10):425-427.
Brenner, Steven E. (1999) Errors in genome annotation. Trends in Genetics 15(4):132-1133.
Cappellen, David et al., (1999) Frequent activating mutations of FGFR3 in human bladder arid cervix carcinomas. Nature Genetics 23(1):18-20.
Chusho, Hideki et al., (2001) Dwarfism and early death in mice lacking C-type Natriuretic Peptide. Proc Natl Acad Sci. 98(7):4016-4021.
Coughlin, Shaun R. et al., (1988) Acidic and basic fibroblast growth factors stimulate tyrosine kinase activity in vivo. J Biol Chem. 263(2):988-993.
Dell'Accio, Francesco et al., (2001) Molecular markers predictive of the capacity of expanded human articular chondrocytes to form stable cartilage in vivo, Arthritis Rheum. 44(7):1608-19.
Doerks, Tobias et al., (1998) Protein annotation: detective work for function prediction. Trends Genet. 14(6):248-250.
Dvorakova, Dana et al., (2001) Changes in the expression of FGFR3 in patients with chronic myeloid leukaemia receiving transplants of allogeneic peripheral blood stem cells_ British Journal Haematology 13(3):832-835.
Eriksson, A. Elisabeth et al., (1991) Three-dimensional structure of human basic fibroblast growth factor. Proc. Natl. Acad. Sci. USA 88:3441-3445 (XP002936511).
Ezzat Shereen et al., (2002) Targeted expression of A Human pituitary tumor-derived isoform of FGF Receptor-4 Recapitulates Pituitary Tumorigenesis. Journal of Clinical Investigation 109(1):69-77.
Faham, Salem et al., (1998) Diversity does make a difference: fibroblast growth factor- Heparin interactions. Curr Opin Struct Biol 8(5):578-586.
Fingl, Edward and Woodbury, Dixon M.(1975) General Principles. In: The Pharmacological Basis of Therapeutics. Fifth edition. Goodman, Louis S. and Gilman, Alfred editors.
Gargiulo, B. J. et al., (2002) Phenotypic modulation of human articular chondrocytes by bistratene A. Eur Cell Mater. 3:9-18.
Givol, David and Yayon, Avner (1992) Complexity of FGF receptors: genetic basis for structural diversity and functional specificity FASEB J. 6(15):3362-3369.
Hecht, H. J. et al., (2000) Structure of fibroblast growth factor 9 shows a symmetric dimmer with unique receptor-and heparin-binding interfaces. Acta Cryst. D57:378-384.
Johnson, Daniel E. And Williams, Lewis T. (1993) Structural and functional diversity in the FGF receptor multigene family. Adv Cancer Res. 60:1-41.
Kirikoshi, Hiroyuki et al., (2000) Molecular cloning and characterization of Human FGF-20 on chromosome 8p21.3-p22. Biochem Biophys Res Commun. 274(2):337-343.
Kuroda, S. et al., (1999) Anabolic effect of aminotemiinally truncated Fibroblast Growth Factor 4 (FGF4) on bone. Bone 25:(4)431-437.
Nakatake, Yuhki et al., (2001) Identification of a novel fibroblast growth factor. FGF-22, preferentially expressed in the inner root sheath of the hair follicle. Biochim Biophys Acta. 1517(3):460-463.
Ngo, J. Thomas et al., (1994) Computational complexity, protein structure prediction, and the Levithal Paradox. In: The Protein Folding Problem and Tertiary Structure Prediction. K. Merz Jr. and S. Le Grand, Editors. 433-506.
Nishimura, Tetsuya et al., (2000) Identification Of A Novel FGF, FGF-21, Preferentially Expressed In The Liver. Biochim Biophys Acta 1492(1):203-206.

Okada-Ban, Mai et al., (2000) Fibroblast growth factor-2. International Journal of Biochemistry & Cell Biology 32 (3):263-267.
Olsen, Shaun K. (2003) Fibroblast growth factor (FGF) homologous factors share structural but not functional homology with FGFs. J Biol Chem. 278(36):34226-342236.
Ornitz, David M. et al., (1996) Receptor specificity of the fibroblast growth factor family. J Biol Chem. 271(25)1 5292-7.
Ornitz, David M. (2000) FGFs, heparan sulfate and FGFRs: Complex interactions essential for development. Bio Essays 22:108-112.
Pellegrini, Luca et al., (2000) Crystal structure of fibroblast growth factor receptor ectodomain bound to ligand and heparin. Nature 407(6807):1029-1034.
Pillai, Omathanu and Panchagnula, Ramesh (2001) Polymers in drug delivery. Curr Opin Chem Biol 5 (4):447-451.
Plotnikov, Alexander N. et al., (1999) Structural basis for FGF receptor dimerization and activation. Cell 98 (5):641-650.
Plotnikov, Alexander N. et al., (2000) Crystal structures of two FGF-FGFR complexes reveal the determinants of ligand-receptor specificity. Cell 101(4): 413-424.
Sahni, Malika et al., (1999) FGF signaling inhibits chondrocyte proliferation and regulates bone development through the STAT-1 pathway Genes Devel.13(11):1361-1366.
Schlessinger, Joseph et al., (2000) Crystal structure of a ternary FGF-FGR-1 Heparin complex reveals a dual role for heparin in FGFR binding and dimerization. Mol Cell 6(3):743-750.
Schmal, H. et al., (2007) bFGF influences human articular chondrocyte differentiation. Cytotherapy 9(2):184-93.
Seno, Masaharu et al., (1990) Carboxyl-terminal structure of basic fibroblast growth factor significantly contributes to its affinity for Heparin. Eur J Biochem. 188:239-245.
Shao, Zhang-Qiang et al., (2006) Effects of intramyocardial administration of slow-release basic fibroblast growth factor on angiogenesis and ventricular remodeling in a rat infarct model. Circ. J. 70(4):471-477.
Skolnik, Jeffrey and Fetrow, Jacquelyn S. (2000) From genes to protein structure and function: novel applications of computational approaches in the genomic era. Trends BioTechnol. 18(1):34-39.
Sleeman, Matthew et al., (2001) Identification of a new fibroblast growth factor receptor, FGFR5. Gene 271 (2):171-182.
Smith, Temple and Zhang, Xiaolin (1997) The challenges of genome sequence annotation or The devil is in the details. Nat Biotechnol. 15(12):1222-1223.
Springer, Barry A. et al., (1994) Identification and Concerted Function of Two Receptors Binding Surfaces on Basic Fibroblast Growth Factor Required for Mitogenesis. The Journal of Biological Chemistry 269(43):26879-26884.
Stauber, Deborah J. et al., (2000) Structural interactions of fibroblast growth factor receptor with its ligands. Proc Natl Acad Sci USA 97(1):49-54.
Vajo, Zoltan et al., (2000) The Molecular and Genetic Basis of Fibroblast Growth Factor Receptor 3 Disorders: The Achondroplasia Family of Skeletal Dysplasias, Muenke Craniosynostosis, and Crouzon Syndrome with Acanthosis Nigricans. Endocrine Rev. 21(1):23-,39.
Wells, James A. (1990) Additivity of mutational effects in proteins. Biochemistry 29(37):8509-8517.
Yamashita, Tetsuo et al., (2000) Identification of a novel fibroblast growth factor, FGF-23, preferentially expressed in the ventrolateral thalamic nucleus of the brain. Biochemical and Biophysical Research Communications 277 (2):494-498.
Yayon, Avner et al., (1991) Cell surface, heparin-like molecules are required for binding of basic fibroblast growth factor to its high affinity receptor. Cell 64(4):841-848.
Yee, Cindy J. et al., (2000) Analysis of fibroblast growth factor receptor 3 S249C mutation in cervical carcinoma. Journal of the National Cancer Institute 92(22):1848-1849.
Zhang, Jiandong et al., (1991) Three-dimensional structure of human basic fibroblast growth factor, a structural homolog of interleukin 1 Beta. Proc Natl Acad Sci. USA 88(8):3446-3450.
Zhu, Hengyi et al., (1995) Glu-96 of basic fibroblast growth factor is essential for high affinity receptor binding. Journal Of Biological Chemistry 270(37):21869-21874.
Zhu, Hengyi et al., (1997) Analysis of high-affinity binding determinants in the receptor binding epitope of basic fibroblast growth factor. Protein Engineering 10(4):417-421.
Carr, M. E. Jr. and Alving, B. M. (1995) Effect of fibrin structure on plasmin-mediated dissolution of plasma clots. Blood Coag. Fibrinol. 6(6):567-573.
Carr, Marcus E. (1988) Fibrin formed in plasma is composed of fibers more massive than those formed from purified fibrinogen. Thromb. Haemost. 59(3):535-539.
Cook, James L. et al., (2003) Biocompatibility of three-dimensional chondrocyte grafts in large tibial defects of rabbits. Am J Vet Res. 64(1):12-20.
Gao, Jizong et al., (2002) Repair of osteochondral defect with tissue-engineered two- phase composite material of injectable calcium phosphate and hyaluronan sponge. Tissue Engin. Part A 8(5):827-837.
Gruber, Reinhard et al., (2002) Platelets stimulate proliferation of bone cells: involvement of platelet-derived growth factor, microparticles and membranes. Clin Oral Implants Res. 13(5):529-535.
Haisch, A. et al. (2000) Preparation of a pure autologous biodegradable fibrin matrix for tissue engineering. Med Biol Eng Comput. 38(6):686-689.
Itokazu, M. et al., (1997) The sustained release of antibiotic from freeze-dried fibrin-antibioticcompound and efficacies in a rat model of osteomyelitis. Infection 25(6):359-363.
Sims, C. Derek et al., (1998) Tissue engineered neocartilage using plasma derived polymer substrates and chondrocytes. Plastic & Recon. Surg. 101(6):1580-1585.
"Young's Modulus." Entry on http://en.wikipedia.org. accessed Oct. 27, 2005. 3 pages.
Bradford, Marion M. (1976) A Rapid and Sensitive Method for the Quantitation of Microgram Quantities of Protein Utilizing the Principle of Protein-Dye Binding. Analytical Biochemistry 72(1-2):248-254.
Matsuda et al. (1995) In Vivo Chondrogenesis in Collagen Sponge Sandwiched by Perichondrium. J. Biomater. Sci. Polymer Ed., vol. 7, No. 3, pp. 221-229.
Fujisato et al. (1996) Effect of basic fibroblast growth factor on cartilage regeneration in chondrocyte-seeded collagen sponge scaffold. Biomaterials, vol. 17, No. 2, pp. 155-162.
Non-Final Office Action mailed Apr. 15, 2010 in connection with U.S. Appl. No. 12/079,629.
Non-Final Office Action mailed Apr. 12, 2010 in connection with U.S. Appl. No. 12/191,490.
Non-Final Office Action mailed Apr. 26, 2010 in connection with U.S. Appl. No. 12/147,042.
Non-Final Office Action mailed Apr. 15, 2010 in connection with U.S. Appl. No. 11/657,042.
International Preliminary Report on Patentability for PCT/US2009/001459, mailed on May 12, 2010.
Netiles et al. (Mar. 2004), "In Situ Crosslinkable Hyaluronan For Articular Cartilage Repair", 50th Annual Meeting of the Orthopaedic Research Society, Paper No. 0202.
Final Office Action for U.S. Appl. No. 11/081,103, mailed Aug. 11, 2010.
Non-final Office Action for U.S. Appl. No. 12/010,984, mailed Aug. 16, 2010.
International Search Report and Written Opinion for PCT/US2010/000108, mailed Aug. 24, 2010.
U.S. Appl. No. 12/881,988, filed Sep. 14, 2010.
U.S. Appl. No. 12/924,132, filed Sep. 21, 2010.
Temenoff et al., "Review: Tissue engineering for regeneration of articular cartilage", Biomaterials 21(2000) pp. 431-440.
Hunziker, "Articular cartilage repair: are the intrinsic biological constraints undermining this process insuperable?", Osteoarthritis and Cartilage 7 (1999) pp. 15-28.

* cited by examiner

CARTILAGE ALLOGRAFT PLUG

RELATED APPLICATIONS

There is no related application.

FIELD OF INVENTION

The present invention is generally directed toward an implant and is more specifically directed toward an allograft implant having a cartilage face and bone body which has been treated to remove cellular debris and proteoglycans and is shaped for an interference fit implantation in a shoulder or knee joint. The implant is provided with channels which allow transport of cellular materials throughout the implant site to stimulate cartilage growth

BACKGROUND OF THE INVENTION

Articular cartilage injury and degeneration present medical problems to the general population which are constantly addressed by orthopedic surgeons. Every year in the United States, over 500,000 arthroplastic or joint repair procedures are performed. These include approximately 125,000 total hip and 150,000 total knee arthroplastics and over 41,000 open arthroscopic procedures to repair cartilaginous defects of the knee.

In the knee joint, the articular cartilage tissue forms a lining which faces the joint cavity on one side and is linked to the subchondral bone plate by a narrow layer of calcified cartilage tissue on the other. Articular cartilage (hyaline cartilage) consists primarily of extracellular matrix with a sparse population of chondrocytes distributed throughout the tissue. Articular cartilage is composed of chondrocytes, type II collagen fibril meshwork, proteoglycans and water. Active chondrocytes are unique in that they have a relatively low turnover rate and are sparsely distributed within the surrounding matrix. The collagens give the tissue its form and tensile strength and the interaction of proteoglycans with water give the tissue its stiffness to compression, resilience and durability. The hyaline cartilage provides a low friction bearing surface over the bony parts of the joint. If the lining becomes worn or damaged resulting in lesions, joint movement may be painful or severely restricted. Whereas damaged bone typically can regenerate successfully, hyaline cartilage regeneration is quite limited because of it's limited regenerative and reparative abilities.

Articular cartilage lesions generally do not heal, or heal only partially under certain biological conditions due to the lack of nerves, blood vessels and a lymphatic system. The limited reparative capabilities of hyaline cartilage usually results in the generation of repair tissue that lacks the structure and biomechanical properties of normal cartilage. Generally, the healing of the defect results in a fibrocartilaginous repair tissue that lacks the structure and biomedical properties of hyaline cartilage and degrades over the course of time. Articular cartilage lesions are frequently associated with disability and with symptoms such as joint pain, locking phenomena and reduced or disturbed function. These lesions are difficult to treat because of the distinctive structure and function of hyaline cartilage. Such lesions are believed to progress to severe forms of osteoarthritis. Osteoarthritis is the leading cause of disability and impairment in middle-aged and older individuals, entailing significant economic, social and psychological costs. Each year, osteoarthritis accounts for as many as 39 million physician visits and more than 500,000 hospitalizations. By the year 2020, arthritis is expected to affect almost 60 million persons in the United States and to limit the activity of 11.6 million persons.

There are many current therapeutic methods being used. None of these therapies has resulted in the successful regeneration of hyaline-like tissue that withstands normal joint loading and activity over prolonged periods. Currently, the techniques most widely utilized clinically for cartilage defects and degeneration are not articular cartilage substitution procedures, but rather lavage, arthroscopic debridement, and repair stimulation. The direct transplantation of cells or tissue into a defect and the replacement of the defect with biologic or synthetic substitutions presently accounts for only a small percentage of surgical interventions. The optimum surgical goal is to replace the defects with cartilage-like substitutes so as to provide pain relief, reduce effusions and inflammation, restore function, reduce disability and postpone or alleviate the need for prosthetic replacement.

Lavage and arthroscopic debridement involve irrigation of the joint with solutions of sodium chloride, Ringer or Ringer and lactate. The temporary pain relief is believed to result from removing degenerative cartilage debris, proteolytic enzymes and inflammatory mediators. These techniques provide temporary pain relief, but have little or no potential for further healing.

Repair stimulation is conducted by means of drilling, abrasion arthroplasty or microfracture. Penetration into the subchondral bone induces bleeding and fibrin clot formation which promotes initial repair, however, the tissue formed is fibrous in nature and not durable. Pain relief is temporary as the tissue exhibits degeneration, loss of resilience, stiffness and wear characteristics over time.

The periosteum and perichondrium have been shown to contain mesenchymal progenitor cells capable of differentiation and proliferation. They have been used as grafts in both animal and human models to repair articular defects. Few patients over 40 years of age obtained good clinical results, which most likely reflects the decreasing population of osteochondral progenitor cells with increasing age. There have also been problems with adhesion and stability of the grafts, which result in their displacement or loss from the repair site.

Transplantation of cells grown in culture provides another method of introducing a new cell population into chondral and osteochondral defects. Carticel® is a commercial process to culture a patient's own cartilage cells for use in the repair of cartilage defects in the femoral condyle marketed by Genzyme Biosurgery in the United States and Europe. The procedure uses arthroscopy to take a biopsy from a healthy, less loaded area of articular cartilage. Enzymatic digestion of the harvested tissue releases the cells that are sent to a laboratory where they are grown for a period ranging from 2-5 weeks. Once cultivated, the cells are injected during a more open and extensive knee procedure into areas of defective cartilage where it is hoped that they will facilitate the repair of damaged tissue. An autologous periosteal flap with cambium layer is used to seal the transplanted cells in place and act as a mechanical barrier. Fibrin glue is used to seal the edges of the flap. This technique preserves the subchondral bone plate and has reported a high success rate. Proponents of this procedure report that it produces satisfactory results, including the ability to return to demanding physical activities, in more than 90% of patients and that biopsy specimens of the tissue in the graft sites show hyaline-like cartilage repair. More work is needed to assess the function and durability of the new tissue and determine whether it improves joint function and delays or prevents joint degeneration. As with the perichondrial graft, patient/donor age may compromise the success of this procedure as chondrocyte population decreases with increasing age. Disadvantages to this procedure include the need for two separate surgical procedures, potential damage to surrounding cartilage when the periosteal patch is sutured in place, the requirement of demanding microsurgical techniques, and the expensive cost of the procedure which is currently not covered by insurance.

Osteochondral transplantation or mosaicplasty involves excising all injured or unstable tissue from the articular defect and creating cylindrical holes in the base of the defect and underlying bone. These holes are filled with autologous cylindrical plugs of healthy cartilage and bone in a mosaic fashion. The osteochondral plugs are harvested from a lower weight-bearing area of lesser importance in the same joint. This technique, shown in Prior Art FIG. 2, can be performed as arthroscopic or open procedures. Reports of results of osteochondral plug autografts in a small numbers of patients indicate that they decrease pain and improve joint function, however, long-term results have not been reported. Factors that can compromise the results include donor site morbidity, effects of joint incongruity on the opposing surface of the donor site, damage to the chondrocytes at the articular margins of the donor and recipient sites during preparation and implantation, and collapse or settling of the graft over time. The limited availability of sites for harvest of osteochondral autografts restricts the use of this approach to treatment of relatively small articular defects and the healing of the chondral portion of the autograft to the adjacent articular cartilage remains a concern.

Transplantation of large allografts of bone and overlying articular cartilage is another treatment option that involves a greater area than is suitable for autologous cylindrical plugs, as well as for a non-contained defect. The advantages of osteochondral allografts are the potential to restore the anatomic contour of the joint, lack of morbidity related to graft harvesting, greater availability than autografts and the ability to prepare allografts in any size to reconstruct large defects. Clinical experience with fresh and frozen osteochondral allografts shows that these grafts can decrease joint pain, and that the osseous portion of an allograft can heal to the host bone and the chondral portion can function as an articular surface. Drawbacks associated with this methodology in the clinical situation include the scarcity of fresh donor material and problems connected with the handling and storage of frozen tissue. Fresh allografts carry the risk of immune response or disease transmission. Musculoskeletal Transplant Foundation (MTF) has preserved fresh allografts in a media that maintains a cell viability of 50% for 35 days for use as implants. Frozen allografts lack cell viability and have shown a decreased amount of proteoglycan content which contribute to deterioration of the tissue.

A number of United States Patents have been specifically directed towards bone plugs which are implanted into a bone defect. Examples of such bone plugs are U.S. Pat. No. 4,950,296 issued Aug. 21, 1990 which discloses a bone graft device comprising a cortical shell having a selected outer shape and a cavity formed therein for receiving a cancerous plug, and a cancellous plug fitted into the cavity in a manner to expose at least one surface; U.S. Pat. No. 6,039,762 issued Mar. 21, 2000 having a cylindrical shell with an interior body of deactivated bone material and U.S. Pat. No. 6,398,811 issued Jun. 4, 2002 directed toward a bone spacer which has a cylindrical cortical bone plug with an internal throughgoing bore designed to hold a reinforcing member. U.S. Pat. No. 6,383,211 issued May 7, 2002 discloses an invertebral implant having a substantially cylindrical body with a throughgoing bore dimensioned to receive bone growth materials.

U.S. Pat. No. 6,379,385 issued Apr. 30, 2002 discloses an implant base body of spongious bone material into which a load carrying support element is embedded. The support element can take the shape of a diagonal cross or a plurality of cylindrical pins. See also, U.S. Pat. No. 6,294,187 issued Sep. 25, 2001 which is directed to a load bearing osteoimplant made of compressed bone particles in the form of a cylinder. The cylinder is provided with a plurality of throughgoing bores to promote blood flow through the osteoimplant or to hold a demineralized bone and glycerol paste mixture. U.S. Pat. No. 6,096,081 issued Aug. 1, 2000 shows a bone dowel with a cortical end cap or caps at both ends, a brittle cancerous body and a throughgoing bore.

A number of patents in the prior art show the use of bone putty, pastes or gels to fill bone defects. U.S. Pat. No. 5,290,558 issued Mar. 1, 1994 discloses a flowable demineralized bone powder composition using an osteogenic bone powder with large particle size ranging from about 0.1 to about 1.2 cm. mixed with a low molecular weight polyhydroxy compound possessing from 2 to about 18 carbons including a number of classes of different compounds such as monosaccharides, disaccharides, water dispersible oligosaccharides and polysaccharides.

A bone gel is disclosed in the U.S. Pat. No. 5,073,373 issued Dec. 17, 1991. Bone lamellae in the shape of threads or filaments retaining low molecular weight glycerol carrier are disclosed in U.S. Pat. No. 5,314,476 issued May 24, 1994 and U.S. Pat. No. 5,507,813 issued Apr. 16, 1996 and the tissue forms described in these patents are known commercially as the GRAFTON® Putty and Flex, respectively.

U.S. Pat. No. 5,356,629 issued Oct. 18, 1994 discloses making a rigid gel in the nature of a bone cement to fill defects in bone by mixing biocompatible particles, preferably polymethylmethacrylate coated with polyhydroxyethylmethacrylate in a matrix selected from a group which lists hyaluronic acid to obtain a molded semi-solid mass which can be suitably worked for implantation into bone. The hyaluronic acid can also be utilized in monomeric form or in polymeric form preferably having a molecular weight not greater than about one million Daltons. It is noted that the nonbioabsorbable material which can be used to form the biocompatible particles can be derived from xenograft bone, homologous bone, autogenous bone as well as other materials. The bioactive substance can also be an osteogenic agent such as demineralized bone powder morselized cancerous bone, aspirated bone marrow and other autogenous bone sources. The average size of the particles employed is preferably about 0.1 to about 3.0 mm, more preferably about 0.2 to about 1.5 mm, and most preferably about 0.3 to about 1.0 mm. It is inferentially mentioned but not taught that particles having average sizes of about 7,000 to 8,000 microns, or even as small as about 100 to 700 microns can be used.

U.S. Pat. No. 4,172,128 issued Oct. 23, 1979 discloses a demineralized bone material mixed with a carrier to reconstruct tooth or bone material by adding a mucopolysaccharide to a mineralized bone colloidal material. The composition is formed from a demineralized coarsely ground bone material, which may be derived from human bones and teeth, dissolved in a solvent forming a colloidal solution to which is added a physiologically inert polyhydroxy compound such as mucopolysaccharide or polyuronic acid in an amount which causes orientation when hydrogen ions or polyvalent metal ions are added to form a gel. The gel will be flowable at elevated temperatures above 35° C. and will solidify when brought down to body temperature. Example 25 of the patent notes that mucopolysaccharides produce pronounced ionotropic effects and that hyaluronic acid is particularly responsible for spatial cross-linking U.S. Pat. No. 6,030,635 issued Feb. 29, 2000 and U.S. Pat. No. 6,437,018 issued Aug. 20, 2002 are directed toward a malleable bone putty and a flowable gel composition for application to a bone defect site to promote new bone growth at the site which utilize a new bone growth inducing compound of demineralized lyophilized allograft bone powder. The bone powder has a particle size ranging from about 100 to about 850 microns and is mixed in a high molecular weight hydrogel carrier which contains a sodium phosphate saline buffer.

The use of implants for cartilage defects is much more limited. Aside from the fresh allograft implants and autologous implants, U.S. Pat. No. 6,110,209 issued Nov. 5, 1998 shows the use an autologous articular cartilage cancellous bone paste to fill arthritic defects. The surgical technique is arthroscopic and includes debriding (shaving away loose or fragmented articular cartilage), followed by morselizing the base of the arthritic defect with an awl until bleeding occurs. An osteochondral graft is then harvested from the inner rim of the intercondylar notch using a trephine. The graft is then morselized in a bone graft crusher, mixing the articular cartilage with the cancerous bone. The paste is then pushed into the defect and secured by the adhesive properties of the bleeding bone. The paste can also be mixed with a cartilage stimulating factor, a plurality of cells, or a biological glue. All patients are kept non-weight bearing for four weeks and used a continuous passive motion machine for six hours each night. Histologic appearance of the biopsies have mainly shown a mixture of fibrocartilage with hyaline cartilage. Concerns associated with this method are harvest site morbidity and availability, similar to the mosaicplasty method.

U.S. Pat. No. 6,379,367 issued Apr. 30, 2002 discloses a plug with a base membrane, a control plug, and a top membrane which overlies the surface of the cartilage covering the defective area of the joint.

SUMMARY OF THE INVENTION

A cartilage allograft construct assembly comprising a plug with a subchondral bone base and cartilage cap for replacing of articular cartilage defects is used together with a milled cartilage in a biocompatible carrier forming a paste or gel which is added to the plug or placed in a bore which has been cut into the patient to remove the lesion defect area. Additives may be applied to the cartilage mixture in order to increase chondrocyte migration and proliferation. Each allograft construct can support the addition of a variety of chondrogenic stimulating factors including, but not limited to growth factors (FGF-2, FGF-5, IGF-1, TGF-β, BMP-2, BMP-7, PDGF, VEGF), human allogenic or autologous chondrocytes, human allogenic or autologous bone marrow cells, stem cells, demineralized bone matrix, insulin, insulin-like growth factor-1, transforming growth factor-B, interleukin-1 receptor antagonist, hepatocyte growth factor, platelet-derived growth factor, Indian hedgehog and parathyroid hormone-related peptide or bioactive glue.

It is an object of the invention to provide an allograft implant for joints which provides pain relief, restores normal function and will postpone or alleviate the need for prosthetic replacement.

It is also an object of the invention to provide a cartilage repair implant which is easily placed in a defect area by the surgeon using an arthroscopic, minimally invasive technique.

It is still another object of the invention to provide an allograft implant which has load bearing capabilities.

It is further an object of the invention to provide an allograft implant procedure which is applicable for both partial and full thickness lesions.

It is yet another object of the invention to provide an allograft implant which facilitates growth of hyaline cartilage.

It is an additional object of the invention to provide implant plugs together with paste and gel formulations that satisfy surgical requirements and are made from available allograft tissue, some of which would otherwise be considered waste and thrown away.

These and other objects, advantages, and novel features of the present invention will become apparent when considered with the teachings contained in the detailed disclosure along with the accompanying drawings.

DESCRIPTION OF THE INVENTION

The term "tissue" is used in the general sense herein to mean any transplantable or implantable tissue, the survivability of which is improved by the methods described herein upon implantation. In particular, the overall durability and longevity of the implant are improved, and host-immune system mediated responses, are substantially eliminated.

The terms "transplant" and "implant" are used interchangably to refer to tissue, material or cells (xenogeneic or allogeneic) which may be introduced into the body of a patient to replace or supplement the structure or function of the endogenous tissue.

The terms "autologous" and "autograft" refer to tissue or cells which originate with or are derived from the recipient, whereas the terms "allogeneic" and "allograft" refer to cells and tissue which originate with or are derived from a donor of the same species as the recipient. The terms "xenogeneic" and "xenograft" refer to cells or tissue which originates with or are derived from a species other than that of the recipient.

The term "gel" refers to a formable mixture of minced or milled pretreated allograft cartilage in a biocomposite carrier having a viscosity which is less than and is less rigid than a mixture of minced or milled pretreated allograft cartilage in a biocompatible carrier referred to by the terms "putty" or "paste" and contains less cartilage by weight than putty or paste.

Figure 5:
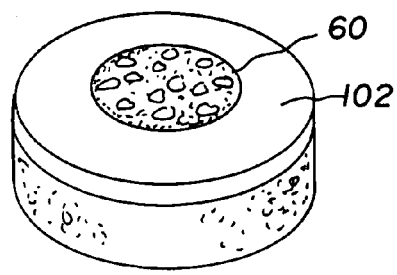
FIG. 5 shows a perspective view of a cylindrical interference fit allograft osteochondral plug assembly having throughgoing bores.
Figure 6:
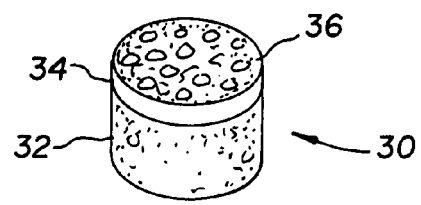
FIG. 6 shows a perspective view of the osteochondral plug used in FIG. 5.

The present invention is directed towards a cartilage repair assembly and method of treatment. The preferred embodiment and best mode of the invention is shown in FIGS. 5 and 6. In the production of the invention, an allograft plug with a cartilage cap and hyaline cartilage are treated to remove cellular material, chondrocytes and pluripotent mesenchymal cells and proteoglycans, freezing same −20° C. to −80° C., and lyophilized reducing its water content.

In the treatment for cell and proteoglycan extraction the allograft cartilage and plugs which were previously harvested from a donor were soaked in hyaluronidase (type IV-s, 3 mg/mL), trypsin (0.25% in monodibasic buffer 3 ml) and the samples were placed in a test tube for 18 hours at 37° C. with sonication. It was found that sonication is not a necessary requirement and the times of soaking vary with concentration of hyaluronidase and trypsin and can be as little as 2 hours. The plug samples were decalcified, washed w/DI water and placed in a 50%/50% chloroform/methanol solution for 72 hours to remove cellular debris and sterilize. The above method has been previously used on human tissue and is set forth in the Journal of Rheumatology, 12:4, 1985 by Gust Verbruggen et al titled Repair Function in Organ Cultured Human Cartilage Replacement of Enzymatically Removed Proteoglycans During Longterm Organ Culture. After repeated washes with sterile DI water, the hydrated plug samples and cartilage were frozen at −70° C. and lyophilized to reduce the water content within the range of about 0.1% to about 8.0%. In an alternative usage, the plug samples and cartilage were frozen after processing.

The osteochondral plug 20 which has been treated as noted above is placed in a bore or core 60 which has been cut in the lesion area of the bone 100 of a patient with the upper surface 25 of the cartilage cap 24 being slightly proud or substantially flush with the surface of the original cartilage 102 remaining at the area being treated. The plug 20 has a subchondral bone portion 22 and an overlying integral cartilage cap 24. The length of the osteochondral plug 20 can be the same as the depth of the bore 60 or less than the depth of the bore 60. If the plug 20 is the same length, the base of the plug implant is supported and the articular cartilage cap 24 is level with the articular cartilage 102. If the plug is of a lesser length, the base of the plug implant is not supported but support is provided by the wall of the bore 60 or respective cut out area as the plug is interference fit within the bore or cut out area with the cap being slightly proud or flush with the articular cartilage 102 depending on the surgeon's preference. With such load bearing support the graft surface is not damaged by weight or bearing loads which can cause micromotion interfering with the graft interface producing fibrous tissue interfaces and subchondral cysts.

Figure 1:
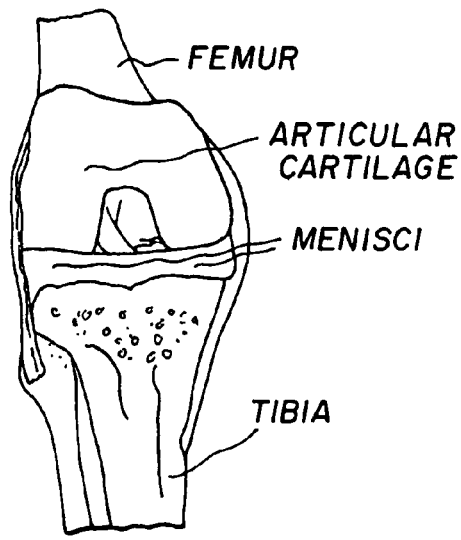
FIG. 1 shows the anatomy of a knee joint.
Figure 2:
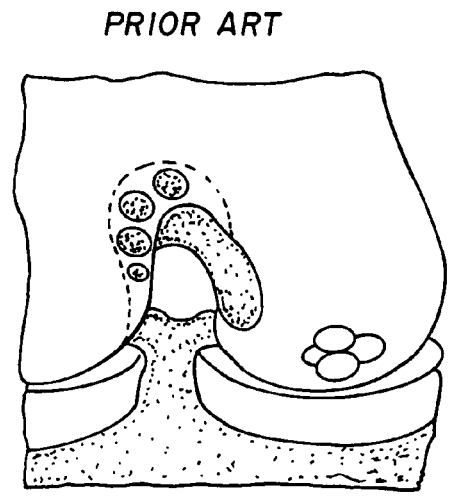
FIG. 2 shows a schematic mosaicplasty as known in the prior art.
Figure 3:
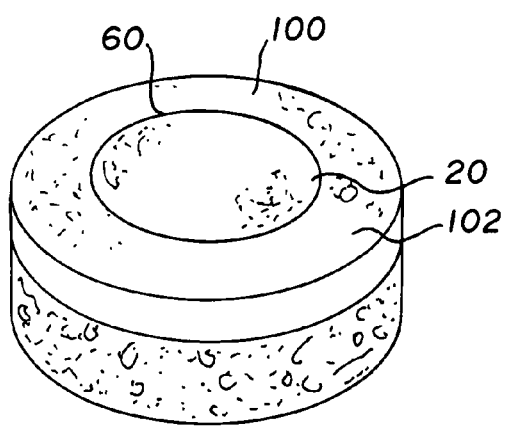
FIG. 3 shows a schematic perspective view of an interference fit cylindrical allograft osteochondral plug assembly in a defect site.
Figure 4:
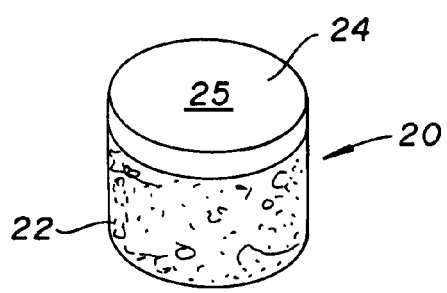
FIG. 4 shows a perspective view of the osteochondral plug used in FIG. 3.

As shown in FIGS. 3 and 5 the respective plug 20, 30 has an interference fit within bore 60. The osteochondral plug, which is generally referred to as a plug in the present description is also envisioned as having various shapes namely; a cylindrical shape 20, 30 as shown in FIGS. 3-6, a mushroom shape 40 as shown in FIGS. 7 and 8, and a channeled or grooved shape 50 as shown in FIG. 9.

The preferred embodiment is shown in FIGS. 5 and 6 and has a cylindrical body 30 with a subchondral bone portion 32 and an overlying cartilage cap 34. A plurality of throughgoing bores 36 are drilled through the bone portion 32 and cap 34 to allow cell migration from a cartilage mixture which has been placed in the bore to promote cartilage growth. The cartilage mixture is more fully described later on in the description of the invention.

Figure 7:
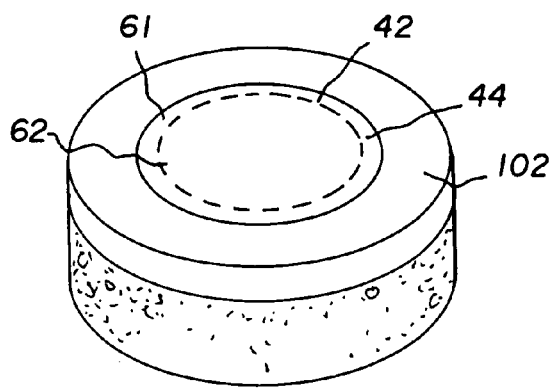
FIG. 7 shows a schematic perspective view of another embodiment of a mushroom shaped allograft osteochondral assembly in a defect site.
Figure 8:
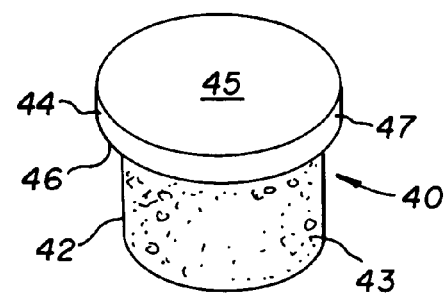
FIG. 8 shows a perspective view of the mushroom shaped osteochondral plug used in FIG. 7.

Another embodiment is a mushroom shaped configuration 40 as is shown in FIGS. 7 and 8 which has a cylindrical subchondral bone portion 42 and an overlying larger diameter cartilage cap 44. The cap 44 is larger in diameter than the body 42 and the periphery 47 of the cap extends past the cylindrical wall 43 of the body. If the cap 44 is the same size as the bore 60 then the body 42 has a length which will engage the floor of the bore 60 so that the cap 44 upper cartilage surface 45 is flush with the upper surface of the surrounding cartilage area 102. Alternately, a second stepped cut 61 may be made in the cartilage surface area down to the depth of the bottom of the cartilage layer which will support the base or lower extending surface 46 of the cap cartilage so that it is flush with the surrounding cartilage area 102 with the lower smaller diameter of the bore 62 being substantially the same as the diameter of the subchondral bone portion with the plug being held therein in an interference fit.

Figure 9:
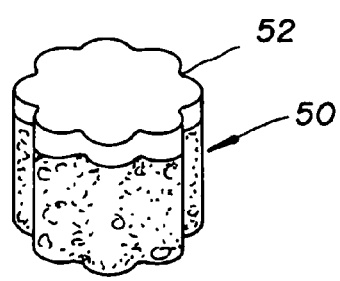
FIG. 9 shows a perspective view of an osteochondral plug with outside longitudinal channels.

As shown in FIG. 9 the exterior surface of the implant 50 may be formed with grooves or channels 52 which can run longitudinally along the outside surface of the implant or alternatively just along the surface of the subchondral bone portion 22, 32, 42 ending at the bottom surface of the cartilage cap 24, 34, 44 overlying same. This variation of FIG. 9 also has an interference fit with the wall of the bore 62.

In operation the lesion or defect is removed by cutting a bore 60 or removing a lesion in the implant area 100 and filling the bore 60 or cut away area with a desired amount of a milled cartilage mixture and a biological carrier such as sodium hyaluronate, hyaluronic acid and its derivatives, gelatin, collagen, chitosan, alginate, buffered PBS, Dextran, or polymers and one or more additives namely chondrogenic stimulating factors including, but not limited to growth factors (FGF-2, FGF-5, IGF-1, TGF-β, BMP-2, BMP-7, PDGF, VEGF), human allogenic or autologous chondrocytes, human allogenic cells, human allogenic or autologous bone marrow cells, human allogenic or autologous stem cells, demineralized bone matrix, insulin, insulin-like growth factor-1, interleukin-1 receptor antagonist, hepatocyte growth factor, platelet-derived growth factor, Indian hedgehog and parathyroid hormone-related peptide. Depending upon the weight of the milled cartilage as noted in Examples 2 and 3 below, the mixture will have the consistency of a paste or gel. The plug 20 is then placed in the bore or cut away area in an interface fit with the surrounding walls.

Suitable organic glue material can be used to keep the implant fixed in place in the implant area. Suitable organic glue material can be found commercially, such as for example; TISSEEL® or TISSUCOL.® (fibrin based adhesive; Immuno AG, Austria), Adhesive Protein (Sigma Chemical, USA), Dow Corning Medical Adhesive B (Dow Corning, USA), fibrinogen thrombin, elastin, collagen, casein, albumin, keratin and the like.

EXAMPLE 1

A non-viable or decellularized osteochondral plug consisting of a subchondral bone base and overlying cartilage cap was treated with a solution or variety of solutions to remove the cellular debris as well as the proteoglycans as noted in the treatment described above. It is believed that this removal provides signaling to stimulate the surrounding chondrocytes to proliferate and form new proteoglycans and other factors producing new matrix. The diameter or diagonal of the plug ranges from 1 mm to 30 mm but is preferably 4 mm to 10 mm which is small enough to fit through the endoscopic cannula, but large enough to minimize the number of plugs needed to fill large defects. This size provides good results at the recipient site and provides a more confluent hyaline surface. The thickness of subchondral bone can be modified to match the anatomy of the patient so that the surface cartilage of the plug will be even with and follow the surface contour of the surface cartilage of the host tissue. The treated plug also creates a more porous matrix, which allows more cells to enter. The plug and minced hyaline cartilage can be stored frozen or freeze dried and support any of the mentioned chondrogenic stimulating factors. The plug can be inserted arthroscopically similar to the mosaicplasty procedure or through an open incision. The plug and cartilage material can be made in various dimensions depending on the size of the defect being treated.

This design uses the allograft cartilage putty or gel as noted below in a prepackaged amount to provide cartilage cell growth for the osteochondral plug. The putty or gel enhances the tissue integration between the plug and host tissue.

The base of the bore or cut away area is provided with a matrix of minced cartilage putty consisting of minced or milled allograft cartilage which has been lyophilized so that its water content ranges from 0.1% to 8.0% ranging from 25% to 50% by weight, mixed with a carrier of sodium hyaluronate solution (HA) (molecular weight ranging from $7.0 \times 10^5$ to $1.2 \times 10^6$) or any other bioabsorbable carrier such as hyaluronic acid and its derivatives, gelatin, collagen, chitosan, alginate, buffered PBS, Dextran, or polymers, the carrier ranging from ranging from 75% to 50% by weight. The cartilage is milled to a size ranging up to 1 mm.

In gel form, the minced cartilage has been lyophilized so that its water content ranges from 0.1% to 8.0%, ranging from 15% to 30% by weight and the carrier ranges from 85% to 70% by weight. The particle size of the cartilage when milled is less than or equal to 1 mm dry. The cartilage pieces can be processed to varying particle sizes and the HA or other carrier can have different viscosities depending on the desired consistency of the putty or gel. This cartilage matrix can be deposited into the cartilage defect arthroscopically and fit into the defect where it is held in place by the implant which is placed over it as a cap.

Cells which have been grown outside the patient are inserted by syringe into the matrix before, during or after deposit of the cartilage matrix into the defect area. Such cells include allogenic or autologous, bone marrow cells, stem cells and chondrocyte cells. The cellular density of the cells preferably ranges from $1.0 \times 10^8$ to $5.0 \times 10^8$ or from about 100 million to about 500 million cells per cc of putty or gel mixture. This composite material can be injected into the cartilage defect arthroscopically as previously noted. This matrix can support the previously mentioned chondrogenic stimulating factors.

The operation of placing the cartilage defect assembly in a cartilage defect, comprises (a) drilling a cylindrical hole in a patient at a site of a cartilage defect to remove the diseased area of cartilage; (b) placing a mixture of milled allograft cartilage in a bioabsorbable carrier in the drilled cylindrical hole; and ©) placing the pretreated implant in the bore over the mixture of the inserted milled allograft cartilage in a bioabsorbable carrier in interference with the wall of the bore to contain the mixture in the cylindrical hole for a predetermined period of time to promote cartilage growth at the defect site.

When using the mushroom shaped embodiment of FIGS. 7 and 8 a second larger diameter bore is cut into the bone around the first bore and the cartilage layer is removed to present a stepped bore forming a seat upon which the lower surface of the overlying portion of the cartilage cap is seated.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims.

What we claim is:

1. A method of placing a preshaped allograft plug assembly in a cartilage defect, said assembly comprising a subchondral bone and an overlying cartilage cap which as been treated to remove cellular debris and proteoglycans and milled cartilage in a carrier comprising the steps of:
    (a) cutting a first cylindrical bore in a patient at a site of a cartilage defect area to remove the cartilage defect;
    (b) cutting a second cylindrical bore to having a diameter greater than the first cylindrical bore a depth which is substantially the same as the depth of a cartilage layer in the defect area to form a stepped bore;
    (c) placing a mixture of milled cartilage in a bioabsorbable carrier in the formed hole; and
    (d) placing a preshaped allograft osteochondral plug having a cross section which engages the walls defining said hole allowing the structure to be placed in an interference fit within said stepped bore with the surface of the cartilage cap being substantially flush with surrounding cartilage.

2. The method of claim 1 wherein the first cylindrical bore and the second cylindrical bore have the same axis.

* * * * *